United States Patent
Angell et al.

(10) Patent No.: US 7,432,289 B2
(45) Date of Patent: Oct. 7, 2008

(54) 5-ACYLAMINO-1,1'-BIPHENYL-4-CARBOXAMIDE DERIVATIVES AND THEIR USE AS P38 KINASE INHIBITORS

(75) Inventors: Richard Martyn Angell, London (GB);
Nicola Mary Aston, Stevenage (GB);
Paul Bamborough, Stevenage (GB);
Mark James Bamford, Harlow (GB);
George Stuart Cockerill, London (GB);
Stephen Sean Flack, London (GB);
Dramane Ibrahim Lainé, Stevenage (GB); Suzanne Joy Merrick, Stevenage (GB); Kathryn Jane Smith, Stevenage (GB); Ann Louise Walker, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 10/492,605

(22) PCT Filed: Oct. 16, 2002

(86) PCT No.: PCT/EP02/11576
§ 371 (c)(1),
(2), (4) Date: Apr. 15, 2004

(87) PCT Pub. No.: WO03/032971
PCT Pub. Date: Apr. 24, 2003

(65) Prior Publication Data
US 2004/0242868 A1    Dec. 2, 2004

(30) Foreign Application Priority Data
Oct. 17, 2002  (GB) ................... 0124939.0

(51) Int. Cl.
A61K 31/44   (2006.01)
A61K 31/04   (2006.01)
A61K 31/34   (2006.01)
A61K 33/44   (2006.01)
C07D 307/02  (2006.01)
C07C 241/00  (2006.01)

(52) U.S. Cl. ............... 514/354; 514/461; 514/741; 514/231.5; 514/256; 514/336; 514/617; 546/310; 546/268.1; 549/491; 549/29; 564/155; 564/161; 544/124

(58) Field of Classification Search ............ 546/310; 514/349, 741, 461; 564/155; 549/491
See application file for complete search history.

(56) References Cited

U.S. PATENT DOCUMENTS

| 4,200,750 A | 4/1980 | Warner et al. |
| 4,968,804 A | 11/1990 | Stanek et al. ............ 546/257 |
| 5,064,832 A | 11/1991 | Stanek et al. ............ 514/256 |
| 5,236,934 A | 8/1993 | VanAtten |
| 5,246,943 A | 9/1993 | Blankley et al. |
| 5,521,213 A | 5/1996 | Prasit et al. |
| 5,534,518 A | 7/1996 | Henrie et al. |
| 5,658,903 A | 8/1997 | Adams et al. |
| 5,858,995 A | 1/1999 | Kawai et al. |
| 5,877,190 A | 3/1999 | Dhainaut et al. ............ 514/337 |
| 5,932,576 A | 8/1999 | Anantanarayan et al. |
| 5,945,418 A | 8/1999 | Bemis et al. |
| 5,977,103 A | 11/1999 | Adams et al. |

(Continued)

FOREIGN PATENT DOCUMENTS

EP    0 533 266    9/1992

(Continued)

OTHER PUBLICATIONS

Boehm et. al., "New Inhibitors of p38 kinase", Expert Opinion on Therapeutic Patents, (2000)10(1), pp. 25-37.*
Hcaplus 135:101738.*
Hanson, Gunnar, "Pulmonary-Allergy, Dermatological, Gastrointestinal & Arthritis Inhibitors of p38 kinase", Expert Opinion on Therapeutic Patents, pp. 729-733, 7(7), (1997).*
Patani et al., "Biososterism: A Rational Approach in Drug Design", Chem. Rev., 96, 3147-3176, 1996.*
West, Anthony R., Solid State Chemistry and its Applications, Wiley, New York, 1998, pp. 358 & 365.*
Boehm et al., Expert Opinion of Therapeutic Patents, vol. 10 (1) pp. 25-37 (2000).
Boehm, et al, Journal of Medicinal Chemistry, vol. 39(20) pp. 3929-3937 (1996).
Ceccarelli et al., European Journal of Medicinal Chemistry, vol. 33 (12) pp. 943-955 (1998).

(Continued)

Primary Examiner—Zinna N Davis
(74) Attorney, Agent, or Firm—Dara L. Dinner; Stephen Venetianer; Charles M. Kinzig

(57) ABSTRACT

Compounds of formula (I):

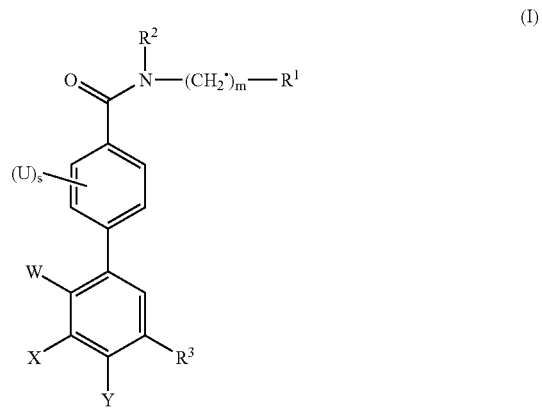

or pharmaceutically acceptable salts or solvates thereof, and their use as pharmaceuticals, particularly as p38 kinase inhibitors.

13 Claims, No Drawings

U.S. PATENT DOCUMENTS

| | | | |
|---|---|---|---|
| 6,060,491 A | 5/2000 | Pruitt et al. | 514/355 |
| 6,080,767 A | 6/2000 | Klein et al. | |
| 6,087,496 A | 7/2000 | Anantanarayan et al. | |
| 6,130,235 A | 10/2000 | Mavunkel et al. | |
| 6,147,080 A | 11/2000 | Bemis et al. | |
| 6,174,887 B1 | 1/2001 | Haruta et al. | |
| 6,251,914 B1 | 6/2001 | Adams et al. | |
| 6,277,989 B1 | 8/2001 | Chakravarty et al. | |
| 6,323,227 B1 | 11/2001 | Klein et al. | |
| 6,392,047 B1 | 5/2002 | Geissler et al. | 546/260 |
| 6,399,627 B1 | 6/2002 | Song et al. | 514/307 |
| 6,420,561 B1 | 7/2002 | Haruta et al. | 544/399 |
| 6,436,925 B1 | 8/2002 | Lubisch et al. | |
| 6,448,257 B1 | 9/2002 | Mavunkel et al. | 514/292 |
| 6,451,794 B1 | 9/2002 | Beswick et al. | |
| 6,498,166 B1 | 12/2002 | Campbell et al. | |
| 6,509,361 B1 | 1/2003 | Weier et al. | |
| 6,509,363 B2 | 1/2003 | Salituro et al. | |
| 6,545,054 B1 | 4/2003 | Song et al. | 514/603 |
| 6,576,632 B1 | 6/2003 | Goldstein et al. | 514/242 |
| 6,579,872 B1 | 6/2003 | Brown et al. | |
| 6,605,625 B2 | 8/2003 | Peukert et al. | 514/333 |
| 6,638,980 B1 | 10/2003 | Su et al. | |
| 6,696,464 B2 | 2/2004 | McClure et al. | 514/303 |
| 6,699,994 B1 | 3/2004 | Babu et al. | 546/306 |
| 6,774,127 B2 | 8/2004 | Adams et al. | |
| 6,794,377 B2 | 9/2004 | Peukert et al. | 514/183 |
| 6,821,965 B1 | 11/2004 | Brown et al. | 514/217.05 |
| 6,855,719 B1 | 2/2005 | Thomas et al. | |
| 6,867,209 B1 | 3/2005 | Mavunkel et al. | 524/253 |
| 6,924,392 B2 | 8/2005 | Peukert et al. | 564/155 |
| 6,936,719 B2 | 8/2005 | Babu et al. | 546/323 |
| 6,956,037 B2 | 10/2005 | Brown et al. | 514/235.5 |
| 7,125,898 B2 * | 10/2006 | Aston et al. | 514/355 |
| 2001/0011135 A1 | 8/2001 | Reidl et al. | |
| 2003/0055088 A1 | 3/2003 | Shao et al. | 514/340 |
| 2003/0139605 A1 | 7/2003 | Riedl et al. | 546/291 |
| 2003/0225089 A1 | 12/2003 | Jung et al. | 514/242 |
| 2004/0038858 A1 | 2/2004 | Dorsch et al. | |
| 2004/0053942 A1 | 3/2004 | Alberti et al. | |
| 2004/0116479 A1 | 6/2004 | Haviv et al. | 514/356 |
| 2004/0128287 A1 | 7/2004 | Barth et al. | 514/419 |
| 2004/0162281 A1 | 8/2004 | Babu et al. | 514/217.03 |
| 2004/0176446 A1 | 9/2004 | Alonso-Alija et al. | |
| 2004/0242868 A1 * | 12/2004 | Angell et al. | 544/59 |
| 2004/0249161 A1 | 12/2004 | Angell et al. | |
| 2004/0254200 A1 | 12/2004 | Davis et al. | 514/260.1 |
| 2004/0266839 A1 | 12/2004 | Angell et al. | |
| 2004/0267012 A1 | 12/2004 | Angell et al. | |
| 2005/0020540 A1 * | 1/2005 | Angell et al. | 514/63 |
| 2005/0020590 A1 | 1/2005 | Lang et al. | 514/230.5 |
| 2005/0038014 A1 | 2/2005 | Angell et al. | |
| 2005/0065195 A1 | 3/2005 | Angell et al. | |
| 2005/0090491 A1 | 4/2005 | Angell et al. | |
| 2005/0176964 A1 | 8/2005 | Aston et al. | 546/268.1 |
| 2007/0129354 A1 * | 6/2007 | Aston et al. | 514/227.5 |

FOREIGN PATENT DOCUMENTS

| | | |
|---|---|---|
| EP | 0 533 268 | 9/1992 |
| EP | 0 849 256 | 6/1998 |
| EP | 0849256 A1 * | 6/1998 |
| EP | 0 346 841 | 6/2003 |
| EP | 0 430 033 | 4/2004 |
| GB | 2 276 161 | 3/1993 |
| GB | 2 276 162 | 3/1993 |
| GB | 2 273 930 | 12/1993 |
| GB | 2 295 387 | 5/1996 |
| JP | 11218884 | 8/1999 |
| WO | WO 94/15920 | 7/1994 |
| WO | WO 95/06636 | 3/1995 |
| WO | WO 95/06644 | 3/1995 |
| WO | WO 95/11243 | 4/1995 |
| WO | WO 95/15954 | 6/1995 |
| WO | WO 95/17401 | 6/1995 |
| WO | WO 95/29907 | 11/1995 |
| WO | WO 95/30675 | 11/1995 |
| WO | WO 96/31508 | 10/1996 |
| WO | WO 96/31509 | 10/1996 |
| WO | WO 97/03034 | 1/1997 |
| WO | WO 98/57934 | 12/1998 |
| WO | 99/32463 | 7/1999 |
| WO | WO 99/32463 | 7/1999 |
| WO | WO 00/12074 | 3/2000 |
| WO | WO 00/12497 | 3/2000 |
| WO | WO 00/26216 | 5/2000 |
| WO | WO 00/56738 | 9/2000 |
| WO | WO 00/71493 | 11/2000 |
| WO | WO 00/71509 | 11/2000 |
| WO | WO 00/71510 | 11/2000 |
| WO | WO 00/71511 | 11/2000 |
| WO | WO 01/27089 | 4/2001 |
| WO | WO 01/34605 | 5/2001 |
| WO | WO 01/70695 | 9/2001 |
| WO | WO 01/87875 | 11/2001 |
| WO | WO 02/40486 | 5/2002 |
| WO | WO 03/032970 | 4/2003 |
| WO | WO 03/068747 | 8/2003 |
| WO | WO 03/093248 | 11/2003 |
| WO | WO 2004/010995 | 2/2004 |
| WO | WO 2004/089874 | 10/2004 |
| WO | WO 2004/089875 | 10/2004 |
| WO | WO 2004/089876 | 10/2004 |
| WO | WO 2005/014550 | 2/2005 |
| WO | WO 05/073189 | 8/2005 |
| WO | WO 05/073217 | 8/2005 |
| WO | WO 05/073219 | 8/2005 |

OTHER PUBLICATIONS

Gabriele et al., *European Journal of Organic Chemistry*, vol. 2001 (24) pp. 4607-4613 (2001).

Han et al., *Biohemica et Biophysica Acta—Molecular Cell Research*, vol. 1265 (2-3) pp. 224-227 (1995.

Hanson, *Expert Opinion on Therapeutic Patents*, vol. 7(7) pp. 729-733 (1997).

Henry et al., *Drugs of the Future*, vol. 24 (12) pp. 1345-1354 (1999).

Jiang et al, *Journal of Biological Chemistry*, vol. 271 (30) pp. 17920-17926 (1996).

Li et al., *Biochemical and Biophysical Research Communications*, vol. 228 (2) pp. 334-340 (1996).

Liebeskind et al., *Organic Letters*, vol. 4 (6) pp. 979-981 (2002).

Moreland et al., *Annals of Internal Medicine*, vol. 130 (6) pp. 478-486 (1999).

Murali Dhar et al., *Bioorganic and Medicinal Chemistry Letters*, vol. 12 (21) pp. 3125-3128 (2002).

Rankin et al., *British Journal of Rheumatology*, vol. 34 pp. 334-342 (1995).

Salituro et al., *Current Medicinal Chemistry*, vol. 6 pp. 807-823 (1999).

Wang et al., *Journal of Biological Chemistry*, vol. 272 (38) pp. 23668-23674 (1997).

Marin et al., Blood, vol. 98(3) pp. 667-673 (2001.

Foster et al., Drug News Perspect., vol. 13(8) pp. 488-497 (2000).

Henry, J. et al., "Potent Inhibitors of the MAP Kinase p. 38", Bioorganic & Medicinal Chemistry Letters 8 (1998) pp. 3335-3340.

Courtney, S. et al., "2,3-Dihydro-1,3-dioxo-1H-isoindole-5-carboxylic aicd derivatives: a novel class of small molecule heparanase inhibitors", Bioorganic & Medicinal Chemistry Letters 14 (2004), pp. 3269-3273.

Boehm, J. et al., "New Inhibitors of p. 38 kinase", Expert Opinion on Therapeutic Patents, 10(1), Ashley Publications, (2000), pp. 25-37.

U.S. Appl. No. 10/513,095, filed Aug. 26, 2005, Angell et al.

U.S. Appl. No. 10/492,714, filed Apr. 15, 2004, Angell et al.

U.S. Appl. No. 10/568,121, filed Feb. 9, 2006, Walker, A.
U.S. Appl. No. 10/522,955, filed Nov. 11, 2005, Angell et al.
U.S. Appl. No. 10/551,503, filed Sep. 30, 2005, Aston, N.
U.S. Appl. No. 10/551,501, filed Sep. 30, 2005, Aston N.
U.S. Appl. No. 10/551,502, filed Sep. 30, 2005, Aston et al.

* cited by examiner

5-ACYLAMINO-1,1'-BIPHENYL-4-CARBOXAMIDE DERIVATIVES AND THEIR USE AS P38 KINASE INHIBITORS

This application is filed pursuant to 35 U.S.C. § 371 as a U.S. National Phase Application of International Application No. PCT/EP02/11576 filed Oct. 16, 2002, which claims priority from GB 0124939.0 filed Oct. 17, 2001.

This invention relates to novel compounds and their use as pharmaceuticals, particularly as p38 kinase inhibitors, for the treatment of certain diseases and conditions.

We have now found a group of novel compounds that are inhibitors of p38 kinase.

According to the invention there is provided a compound of formula (I):

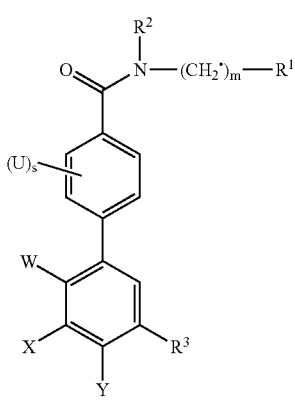

(I)

when m is 0 to 4 $R^1$ is selected from $C_{1-6}$alkyl, $C_{3-7}$cycloalkyl, $C_{2-6}$alkenyl, $-SO_2NR^4R^5$, $-CONR^4R^5$ and $-COOR^4$;

and when m is 2 to 4 $R^1$ is additionally selected from $C_{1-6}$alkoxy, hydroxy, $NR^4R^5$, $-NR^4SO_2R^5$, $-NR^4SOR^5$, $-NR^4COR^5$, and $-NR^4CONR^4R^5$;

$R^2$ is selected from hydrogen, $C_{1-6}$alkyl and $-(CH_2)_n-C_{3-7}$cycloalkyl;

$R^3$ is the group $-NH-CO-R^6$;

$R^4$ and $R^5$ are independently selected from hydrogen, $C_{1-6}$alkyl, heterocyclyl optionally substituted by $C_{1-4}$alkyl, and phenyl wherein the phenyl is optionally substituted by up to two groups independently selected from $C_{1-6}$alkoxy, $C_{1-6}$alkyl and halogen; or $R^4$ and $R^5$, together with the nitrogen atom to which they are bound, form a five- to six-membered heterocyclic or heteroaryl ring optionally containing one additional heteroatom selected from oxygen, sulfur and nitrogen, wherein the ring may be substituted by up to two $C_{1-6}$alkyl groups;

$R^6$ is selected from hydrogen, $C_{1-6}$alkyl, $C_{1-6}$alkoxy, $-(CH_2)_p-C_{3-7}$cycloalkyl, trifluoromethyl, $-(CH_2)_q$phenyl optionally substituted by $R^7$ and/or $R^8$, $-(CH_2)_q$heteroaryl optionally substituted by $R^7$ and/or $R^8$, $-(CH_2)_q$heterocyclyl optionally substituted by $R^7$ and/or $R^8$ and $-(CH_2)_q$fused bicyclyl optionally substituted by $R^7$ and/or $R^8$;

$R^7$ is selected from $C_{1-6}$alkyl, $C_{1-6}$alkoxy, $-(CH_2)_p-C_{3-7}$cycloalkyl, $-CONR^9R^{10}$, $-NHCOR^{10}$, $-SO_2NHR^9$, $-NHSO_2R^{10}$, halogen, $-(CH_2)_r NR^{11}R^{12}$, oxy, trifluoromethyl, phenyl optionally substituted by one or more $R^8$ groups and heteroaryl wherein the heteroaryl may be optionally substituted by one or more $R^8$ groups;

$R^8$ is selected from $C_{1-6}$alkyl, $C_{1-6}$alkoxy, halogen, trifluoromethyl and $-NR^{11}R^{12}$;

or $R^7$ and $R^8$, together with the carbon atoms to which they are bound, form a five- or six-membered saturated or unsaturated ring to give a fused bicyclic ring system, wherein the ring that is formed by $R^7$ and $R^8$ may optionally contain one or two heteroatoms selected from oxygen, nitrogen and sulfur;

$R^9$ is selected from hydrogen, $C_{1-6}$alkyl and phenyl wherein the phenyl group may be optionally substituted by one or more $R^8$ groups;

$R^{10}$ is selected from hydrogen and $C_{1-6}$alkyl;

or $R^9$ and $R^{10}$, together with the nitrogen atom to which they are bound, form a five- to six-membered heterocyclic ring optionally containing one additional heteroatom selected from oxygen, sulfur and $N-R^x$, wherein the ring may be substituted by up to two $C_{1-6}$alkyl groups;

$R^x$ is selected from hydrogen and methyl;

$R^{11}$ is selected from hydrogen, $C_{1-6}$alkyl and $-(CH_2)_p-C_{3-7}$cycloalkyl optionally substituted by $C_{1-6}$alkyl;

$R^{12}$ is selected from hydrogen and $C_{1-6}$alkyl; or $R^{11}$ and $R^{12}$, together with the nitrogen atom to which they are bound, form a three- to seven-membered heterocyclic ring optionally containing one additional heteroatom selected from oxygen, sulfur and $N-R^x$, wherein the ring may contain up to one double bond and the ring may be substituted by one or more $R^{13}$ groups;

$R^{13}$ is selected from $C_{1-6}$alkyl, oxy, $-CH_2OC_{1-6}$alkyl, trichloromethyl and $-N(C_{1-6}alkyl)_2$;

U is selected from methyl and halogen;

W is selected from methyl and chlorine;

X and Y are each selected independently from hydrogen, methyl and halogen;

m is selected from 0, 1, 2, 3 and 4 wherein each carbon atom of the resulting carbon chain may be optionally substituted with one or two groups selected independently from $C_{1-6}$alkyl optionally substituted by up to three halogens;

n, p and q are independently selected from 0 and 1;

r is selected from 0, 1, 2 and 3;

s is selected from 0, 1 and 2;

or a pharmaceutically acceptable salt or solvate thereof.

According to a further embodiment of the invention there is provided a compound of formula (IA):

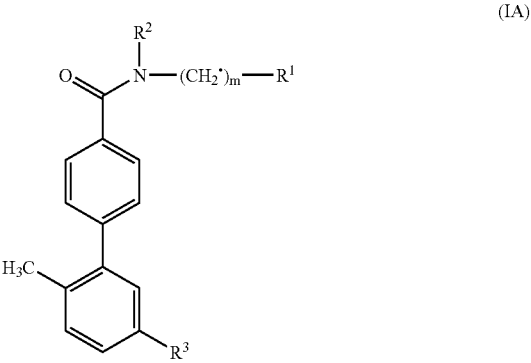

(IA)

wherein $R^1$, $R^2$, $R^3$ and m are as defined above, or a pharmaceutically acceptable salt or solvate thereof.

In a preferred embodiment, the molecular weight of a compound of formula (I) does not exceed 1000, more preferably 800, even more preferably 600.

In a preferred embodiment, $R^1$ is selected from $C_{1-4}$alkyl, in particular, methyl or iso-propyl, $C_{3-6}$cycloalkyl, in particular cyclopropyl, cyclobutyl, cyclopentyl or cyclohexyl, —CONHCH$_3$, —SO$_2$NH$_2$, —SO$_2$N(CH$_3$)$_2$, methoxy, —NHSO$_2$CH$_3$ and —NHCOCH$_3$. In a further preferred embodiment, $R^1$ is selected from $C_{3-6}$cycloalkyl, in particular cyclopropyl; hydroxy; $NR^4R^5$, in particular —N(CH$_3$)$_2$; and —$NR^4SO_2R^5$, in particular —NHSO$_2$CH$_3$.

In a preferred embodiment, $R^2$ is selected from hydrogen, $C_{1-4}$alkyl and —CH$_2$-cyclopropyl, more preferably hydrogen.

In a preferred embodiment, $R^4$ and $R^5$ are independently selected from hydrogen, $C_{1-4}$alkyl and phenyl. Particularly preferred are hydrogen and methyl.

In a preferred embodiment, $R^6$ is selected from —(CH$_2$)$_q$phenyl optionally substituted by $R^7$ and/or $R^8$ and —(CH$_2$)$_q$heteroaryl optionally substituted by $R^7$ and/or $R^8$. In a further preferred embodiment, $R^6$ is selected from $C_{1-4}$alkyl, in particular methyl, ethyl, n-propyl or isobutyl; —(CH$_2$)$_p$—$C_{3-6}$cycloalkyl, in particular cyclopropyl, —CH$_2$-cyclopropyl, cyclobutyl or cyclopentyl; trifluoromethyl; —(CH$_2$)$_q$phenyl optionally substituted by $R^7$ and/or $R^8$; —(CH$_2$)$_q$heteroaryl optionally substituted by $R^7$ and/or $R^8$, in particular furyl, —CH$_2$-furyl, thienyl, thiazolyl, isoxazolyl, pyrazolyl, pyridyl, pyrimidinyl or pyrazinyl optionally substituted by $R^7$ and/or $R^8$; —(CH$_2$)$_q$heterocyclyl optionally substituted by $R^7$ and/or $R^8$ in particular tetrahydrofuranyl and tetrahydropyranyl; and —(CH$_2$)$_q$fused bicyclyl optionally substituted by $R^7$ and/or $R^8$ in particular quinolyl.

In a preferred embodiment, $R^7$ is selected from $C_{1-4}$alkyl, halogen, —$NR^{11}R^{12}$, $C_{3-6}$cycloalkyl, phenyl optionally substituted by one or more $R^8$ groups and heteroaryl optionally substituted by one or more $R^8$ groups. In a further preferred embodiment, $R^7$ is selected from $C_{1-4}$alkyl, in particular methyl or ethyl; $C_{1-4}$alkoxy, in particular methoxy; —(CH$_2$)$_p$—$C_{3-6}$cycloalkyl, in particular cyclopropyl or cyclohexyl; halogen, in particular chlorine; —(CH$_2$)$_r$NR$^{11}$R$^{12}$; phenyl optionally substituted by one or more $R^8$ groups; and heteroaryl, in particular furyl, thienyl, pyrrolyl or pyridyl, wherein the heteroaryl may be optionally substituted by one or more $R^8$ groups. In a preferred embodiment, $R^8$ is selected from $C_{1-2}$alkyl and halogen. In a further preferred embodiment, $R^8$ is selected from $C_{1-2}$alkyl, in particular methyl; halogen, in particular fluorine or chlorine; trifluoromethyl and —$NR^{11}R^{12}$.

In a preferred embodiment, $R^9$ is selected from hydrogen and $C_{1-4}$alkyl.

In a preferred embodiment, $R^{10}$ is selected from hydrogen and $C_{1-4}$alkyl.

In a preferred embodiment, $R^{11}$ is selected from hydrogen, $C_{1-4}$alkyl, $C_{3-6}$cycloalkyl and —CH$_2$C$_{3-6}$cycloalkyl. In a further preferred embodiment, $R^{11}$ is selected from hydrogen; $C_{1-4}$alkyl, in particular methyl, ethyl or isobutyl; and —(CH$_2$)$_p$—$C_{3-6}$cycloalkyl in particular cyclopropyl, —CH$_2$-cyclopropyl, cyclobutyl or cyclohexyl.

In a preferred embodiment, $R^{12}$ is selected from hydrogen and $C_{1-4}$alkyl.

In a preferred embodiment, $R^{11}$ and $R^{12}$, together with the nitrogen atom to which they are bound, form a five- to six-membered heterocyclic ring optionally containing one additional heteroatom selected from oxygen, sulfur and N—$R^x$, wherein $R^x$ is hydrogen or methyl, and the ring may be substituted by one or more $R^{13}$ groups. In a further preferred embodiment, $R^{11}$ and $R^{12}$, together with the nitrogen atom to which they are bound, form a 1,2,3,6-tetrahydropyridyl.

In a preferred embodiment, $R^{13}$ is selected from methyl and oxy. In a further preferred embodiment, $R^{13}$ is selected from $C_{1-4}$alkyl, in particular methyl; oxy; —CH$_2$OC$_{1-4}$alkyl, in particular —CH$_2$OCH$_3$; and —N(C$_{1-6}$alkyl)$_2$, in particular —N(CH$_3$)$_2$.

In a preferred embodiment, W is methyl.

In a preferred embodiment, X and Y are each selected independently from hydrogen, chlorine and fluorine. In a further preferred embodiment, X is fluorine.

In a preferred embodiment, m is selected from 0, 1 and 2, and when the carbon chain of m is substituted, these substituents are preferably one or two methyl and/or fluoro groups. In another preferred embodiment, m is selected from 0, 1 and 2 wherein each carbon atom of the resulting carbon chain may be optionally substituted with one or two groups selected independently from $C_{1-6}$alkyl. In a further preferred embodiment, m is selected from 0, 1, 2, 3 and 4, and when the carbon chain of m is substituted, these substituents are preferably one or two methyl groups.

In a preferred embodiment, n is selected from 0, and 1.

In a preferred embodiment, p is 0.

In a preferred embodiment, q is 0.

In a preferred embodiment, r is selected from 0, 1 and 2.

In a preferred embodiment, s is selected from 0 and 1. In particular, s is 0.

It is to be understood that the present invention covers all combinations of particular and preferred groups described hereinabove.

Particular compounds according to the invention include those mentioned in the examples and their pharmaceutically acceptable salts and solvates. Specific examples which may be mentioned include:

N-(4'-{[(Cyclopropylmethyl)amino]carbonyl}-6-methyl-1,1'-biphenyl-3-yl)-3-furamide;

N-(4'-{[(Cyclopropylmethyl)amino]carbonyl}-6-methyl-1,1'-biphenyl-3-yl)-2-piperidin-1-ylquinoline-4-carboxamide;

N-(4'-{[(Cyclopropylmethyl)amino]carbonyl}-6-methyl-1,1'-biphenyl-3-yl)-2-pyrrolidin-1-ylisonicotinamide;

N-(4'-{[(Cyclopropylmethyl)amino]carbonyl}-6-methyl-1,1'-biphenyl-3-yl)-2-morpholin-4-ylisonicotinamide;

N-(4'-{[(Cyclopropylmethyl)amino]carbonyl}-6-methyl-1,1'-biphenyl-3-yl)-2-piperidin-1-ylisonicotinamide;

N-(4'-{[(Cyclopropylmethyl)amino]carbonyl}-6-methyl-1,1'-biphenyl-3-yl)-2-dimethylaminoisonicotinamide;

2-(Cyclopropylmethylamino)-N-(4'-{[(cyclopropylmethyl)amino]carbonyl}-6-methyl-1,1'-biphenyl-3-yl)isonicotinamide;

N-(4'-{[(Cyclopropylmethyl)amino]carbonyl}-6-methyl-1,1'-biphenyl-3-yl)-2-(isobutylamino)isonicotinamide;

N-(4'-{[(Cyclopropylmethyl)amino]carbonyl}-6-methyl-1,1'-biphenyl-3-yl)-2-thiomorpholin-4-ylisonicotinamide;

2-(Cyclohexylamino)-N-(4'-{[(cyclopropylmethyl)amino]carbonyl}-6-methyl-1,1'-biphenyl-3-yl)isonicotinamide;

2-(Cyclopropylamino)-N-(4'-{[(cyclopropylmethyl)amino]carbonyl}-6-methyl-1,1'-biphenyl-3-yl)isonicotinamide;

N-(4'-{[(Cyclopropylmethyl)amino]carbonyl}-6-methyl-1,1'-biphenyl-3-yl)-2-(diethylamino)isonicotinamide;

N-(4'-{[(Cyclopropylmethyl)amino]carbonyl}-6-methyl-1,1'-biphenyl-3-yl)-2-(4-methylpiperidin-1-yl)isonicotinamide;

N-(4'-{[(Cyclopropylmethyl)amino]carbonyl}-6-methyl-1,1'-biphenyl-3-yl)-2-(2-methylpyrrolidin-1-yl)isonicotinamide;
N-(4'-{[(Cyclopropylmethyl)amino]carbonyl}-6-methyl-1,1'-biphenyl-3-yl)-2-(1,2,3,6-tetrahydropyrid-1-yl)isonicotinamide;
N-(4'-{[(Cyclopropylmethyl)amino]carbonyl}-6-methyl-1,1'-biphenyl-3-yl)-2-(3-methylpiperidin-1-yl)isonicotinamide;
N-(4'-{[(Cyclopropylmethyl)amino]carbonyl}-6-methyl-1,1'-biphenyl-3-yl)-2-(3,5-dimethylpiperidin-1-yl)isonicotinamide;
N-(4'-{[(Cyclopropylmethyl)amino]carbonyl}-6-methyl-1,1'-biphenyl-3-yl)-2-(2-methoxymethylpyrrolidin-1-yl)isonicotinamide;
2-(Cyclobutylamino)-N-(4'-{[(Cyclopropylmethyl)amino]carbonyl}-6-methyl-1,1'-biphenyl-3-yl)isonicotinamide;
N-{4'-[(Cyclopropylamino)carbonyl]-6-methyl-1,1'-biphenyl-3-yl}-2-pyrrolidin-1-ylisonicotinamide;
N-(4'-{[(Cyclopropylmethyl)amino]carbonyl}-6-methyl-1,1'-biphenyl-3-yl)-5-(pyrid-2-yl)thiophene-2-carboxamide;
N-(4'-{[(Cyclopropylmethyl)amino]carbonyl}-6-methyl-1,1'-biphenyl-3-yl)-2-(pyrid-3-yl)thiazole-4-carboxamide;
N-(4'-{[(Cyclopropylmethyl)amino]carbonyl}-6-methyl-1,1'-biphenyl-3-yl)-2-furamide;
N-(4'-{[(Cyclopropylmethyl)amino]carbonyl}-6-methyl-1,1'-biphenyl-3-yl)-thiophene-3-carboxamide;
N-(4'-{[(Cyclopropylmethyl)amino]carbonyl}-6-methyl-1,1'-biphenyl-3-yl)isoxazole-5-carboxamide;
N-(4'-{[(Cyclopropylmethyl)amino]carbonyl}-6-methyl-1,1'-biphenyl-3-yl)-3-(2,5-dimethylpyrrol-1-yl)benzamide;
N-(4'-{[(Cyclopropylmethyl)amino]carbonyl}-6-methyl-1,1'-biphenyl-3-yl)-4-methoxy-3-phenylbenzamide;
N-(4'-{[(Cyclopropylmethyl)amino]carbonyl}-6-methyl-1,1'-biphenyl-3-yl)-3-(2oxo-1-pyrrolidine)benzamide;
N-(4'-{[(Cyclopropylmethyl)amino]carbonyl}-6-methyl-1,1'-biphenyl-3-yl)-3-fur-3-ylbenzamide;
2-Cyclohexyl-N-(4'-{[(cyclopropylmethyl)amino]carbonyl}-6-methyl-1,1'-biphenyl-3-yl)-6-methylquinoline4-carboxamide;
2-Cyclopropyl-N-(4'{[(cyclopropylmethyl)amino]carbonyl}-6-methyl-1,1'-biphenyl-3-yl)quinoline-4-carboxamide;
N-(4'-{[(Cyclopropylmethyl)amino]carbonyl}-6-methyl-1,1'-biphenyl-3-yl)-2-fur-2-ylquinoline4-carboxamide;
N-(4'-{[(Cyclopropylmethyl)amino]carbonyl}-6-methyl-1,1'-biphenyl-3-yl)-6-(4-fluorophenyl)pyrazine-2-carboxamide;
N-(4'-{[(Cyclopropylmethyl)amino]carbonyl}-6-methyl-1,1'-biphenyl-3-yl)-6-morpholin-4-ylpyrazine-2-carboxamide;
N-(4'-{[(Cyclopropylmethyl)amino]carbonyl}-6-methyl-1,1'-biphenyl-3-yl)thiophene-2-carboxamide;
N-(4'-{[(Cyclopropylmethyl)amino]carbonyl}-6-methyl-1,1'-biphenyl-3-yl)benzamide; and
N-(4'-{[(Cyclopropylmethyl)amino]carbonyl}-6-methyl-1,1'-biphenyl-3-yl)-5-(3-chlorophenyl)-2-furamide.

A further specific example which may be mentioned is N-(6-chloro-4'-{[(cyclopropylmethyl)amino]carbonyl}-1,1'-biphenyl-3-yl)-3-furamide.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, isopropyl and t-butyl. A $C_{1-4}$alkyl group is preferred, for example methyl, ethyl, or isopropyl. The said alkyl groups may be optionally substituted with one or more halogen atoms, in particular fluorine atoms, for example, trifluoromethyl.

As used herein, the term "alkoxy" refers to a straight or branched chain alkoxy group, for example, methoxy, ethoxy, propoxy, prop2-oxy, butoxy, but-2-oxy, 2-methylprop-1-oxy, 2-methylprop2-oxy, pentoxy, or hexyloxy. A $C_{1-4}$alkoxy group is preferred, for example methoxy or ethoxy.

As used herein, the term "cycloalkyl" refers to a non-aromatic hydrocarbon ring containing the specified number of carbon atoms which may optionally contain up to one double bond. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{3-6}$cycloalkyl group is preferred, for example, cyclopropyl, cyclopentyl or cyclohexyl. When $R^1$ is a $C_{3-7}$cycloalkyl group, the cycloalkyl group may be optionally substituted by one or more groups selected from $C_{1-6}$alkyl and phenyl, or the $C_{3-7}$cycloalkyl group may be optionally substituted by two adjacent $C_{1-6}$alkyl groups, which together with the carbon atoms to which they are bound, form a fused bicyclic ring system.

As used herein, the term "alkenyl" refers to straight or branched hydrocarbon chains containing the specified number of carbon atoms and containing at least one double bond. For example, $C_{2-6}$alkenyl means a straight or branched alkenyl containing at least 2, and at most 6, carbon atoms and containing at least one double bond.

Examples of "alkenyl" as used herein include, but are not limited to ethenyl and propenyl.

As used herein, the terms "heteroaryl" ring and "heteroaryl" refer to a monocyclic five-to seven-membered unsaturated hydrocarbon ring containing at least one heteroatom independently selected from oxygen, nitrogen and sulfur. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. The said ring may be optionally substituted by one or more substituents independently selected from $C_{1-6}$alkyl and oxy.

As used herein, the terms "heterocyclic ring" and "heterocyclyl" refer to a monocyclic three- to seven-membered saturated or non-aromatic, unsaturated hydrocarbon ring containing at least one heteroatom independently selected from oxygen, nitrogen and sulfur. Preferably, the heterocyclyl ring has five or six ring atoms. Examples of heterocyclyl groups include, but are not limited to, aziridinyl, pyrrolinyl, pyrrolidinyl, imidazolinyl, imidazolidinyl, pyrazolinyl, pyrazolidinyl, piperidyl, piperazinyl, morpholino, tetrahydropyranyl, tetrahydrofuranyl, and thiomorpholino. The said ring may be optionally substituted by one or more substituents independently selected from $C_{1-6}$alkyl and oxy.

As used herein, the terms "fused bicyclic ring system" and "fused bicyclyl" refer to a ring system comprising two five- to seven-membered saturated or unsaturated rings, the ring system optionally containing one or more heteroatoms independently selected from oxygen, nitrogen and sulfur. Preferably, each ring has five or six ring atoms. Examples of suitable fused bicyclic rings include, but are not limited to, naphthyl, indolyl, indolinyl, benzothienyl, quinolyl, isoquinolyl, tetrahydroquinolyl, benzodioxanyl, indanyl and tetrahydronaphthyl. Each ring may be optionally substituted with one or more substituents independently selected from halogen, $C_{1-6}$alkyl, oxy, —$(CH_2)_nNR^{11}R^{12}$, —$CO(CH_2)_n NR^{10}R^{11}$, and imidazolyl. Particularly preferred substituents are chlorine, imidazolyl and —$CH_2$—$N(CH_3)_2$.

As used herein, the terms "halogen" or "halo" refer to the elements fluorine, chlorine, bromine and iodine. Preferred halogens are fluorine, chlorine and bromine. A particularly preferred halogen is fluorine or chlorine.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

Salts of the compounds of the present invention are also encompassed within the scope of the invention and may, for example, comprise acid addition salts resulting from reaction of an acid with a nitrogen atom present in a compound of formula (I). Salts encompassed within the term "pharmaceutically acceptable salts" refer to non-toxic salts of the compounds of this invention. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Gfutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. Other salts which are not pharmaceutically acceptable may be useful in the preparation of compounds of this invention and these form a further aspect of the invention.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

For example, a general method (A) for preparing the compounds of Formula (I) comprises the reactions set out in Scheme 1 below.

Scheme 1

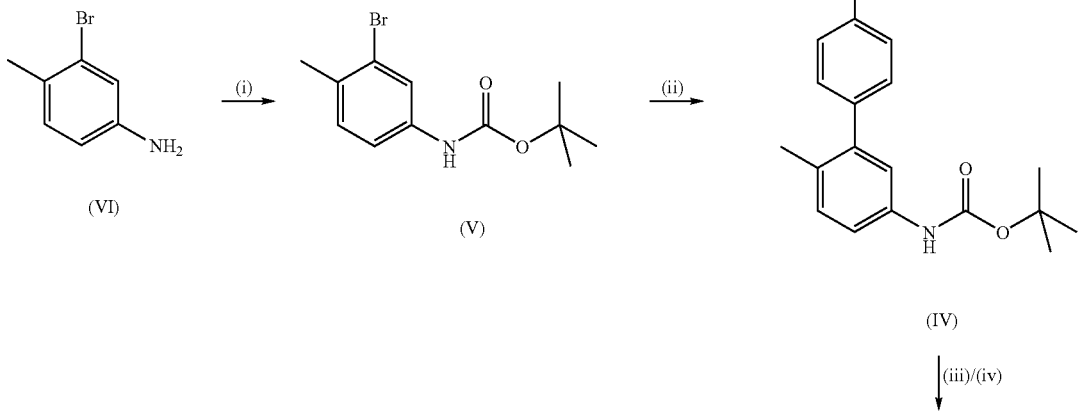

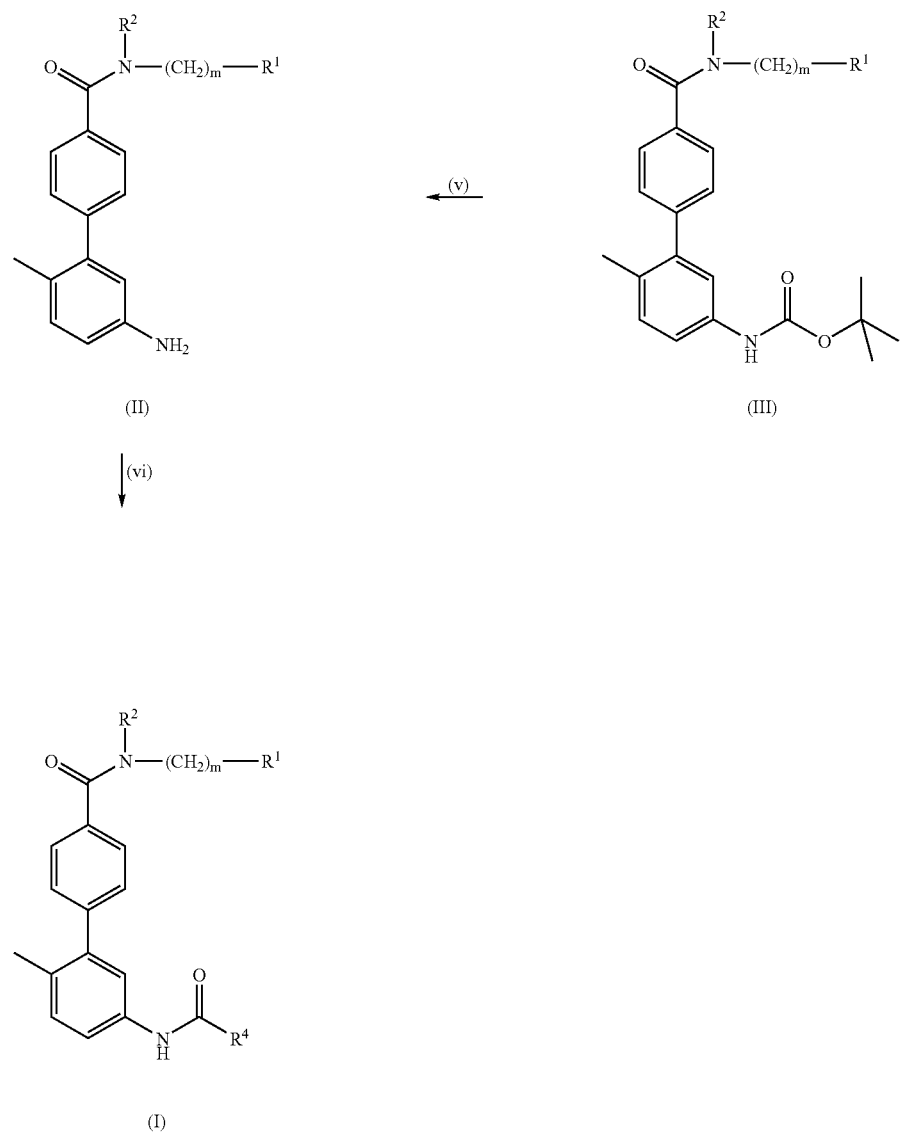
(i) Di-t-butyldicarbonate, Et$_3$N, DCM
(ii) (4-Methoxycarbonylphenyl)boronic acid, (Ph$_3$P)$_4$Pd, CsCO$_3$, DME
(iii) LiOH, THF, H$_2$O
(iv) R$^1$(CH$_2$)$_m$N R$^2$H, HATU, DIPEA, THF
(v) R$^4$COOH, HATU, DIPEA, DMF
For example, a general method (B) for preparing the compounds of Formula (I) comprises the reactions set out in Scheme 2 below.

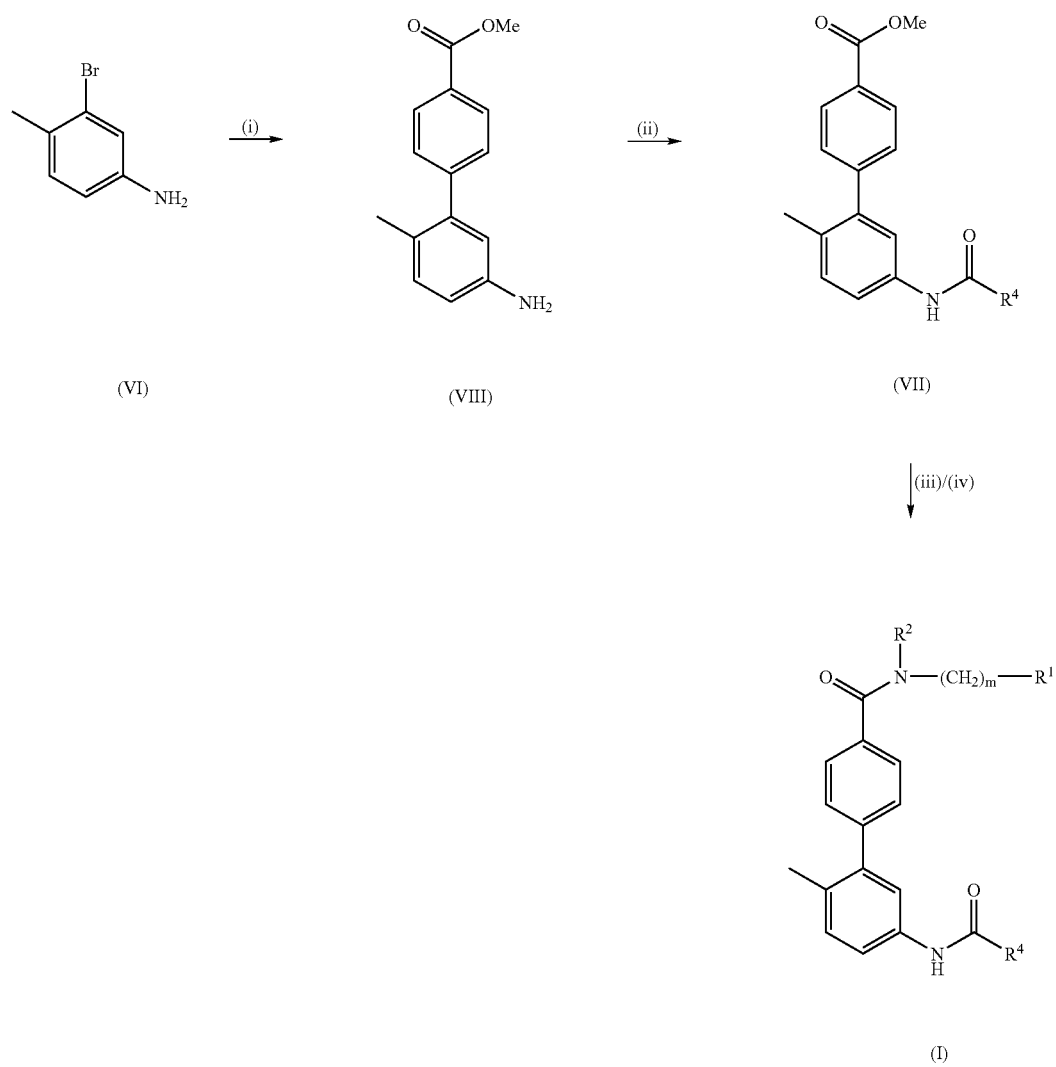
(i) (4-Methoxycarbonylphenyl)boronic acid, (Ph₃P)₄Pd, CsCO₃, DME
(ii) R⁴COOH, HATU, DIPEA, DMF
(iii) LiOH, THF, H₂O
(iv) R¹(CH₂)ₘN R²H, HATU, DIPEA, THF
For example, a general method (C) for preparing the compounds of Formula (I) wherein $R^4$ is
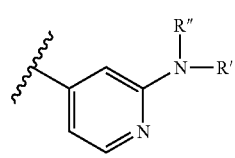
comprises the reactions set out in Scheme 3 below.

Scheme 3
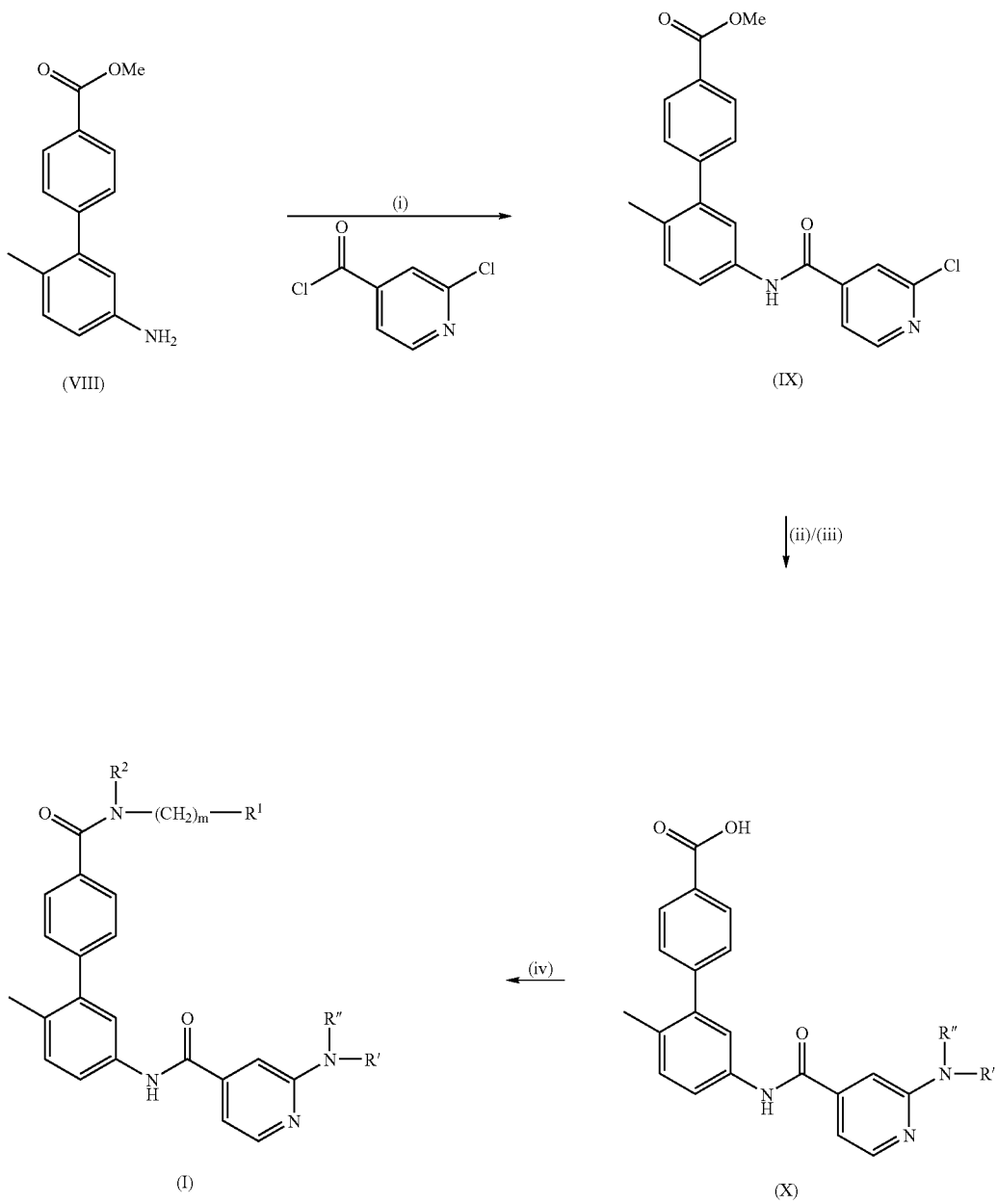
(i) Et₃N, DCM
(ii) LiOH, THF, H₂O
(iii) R'R"NH
(iv) R¹(CH₂)ₘN R²H, HATU, DIPEA, THF
For example, a general method (D) for preparing the compounds of Formula (I) comprises the reactions set out in Scheme 4 below.

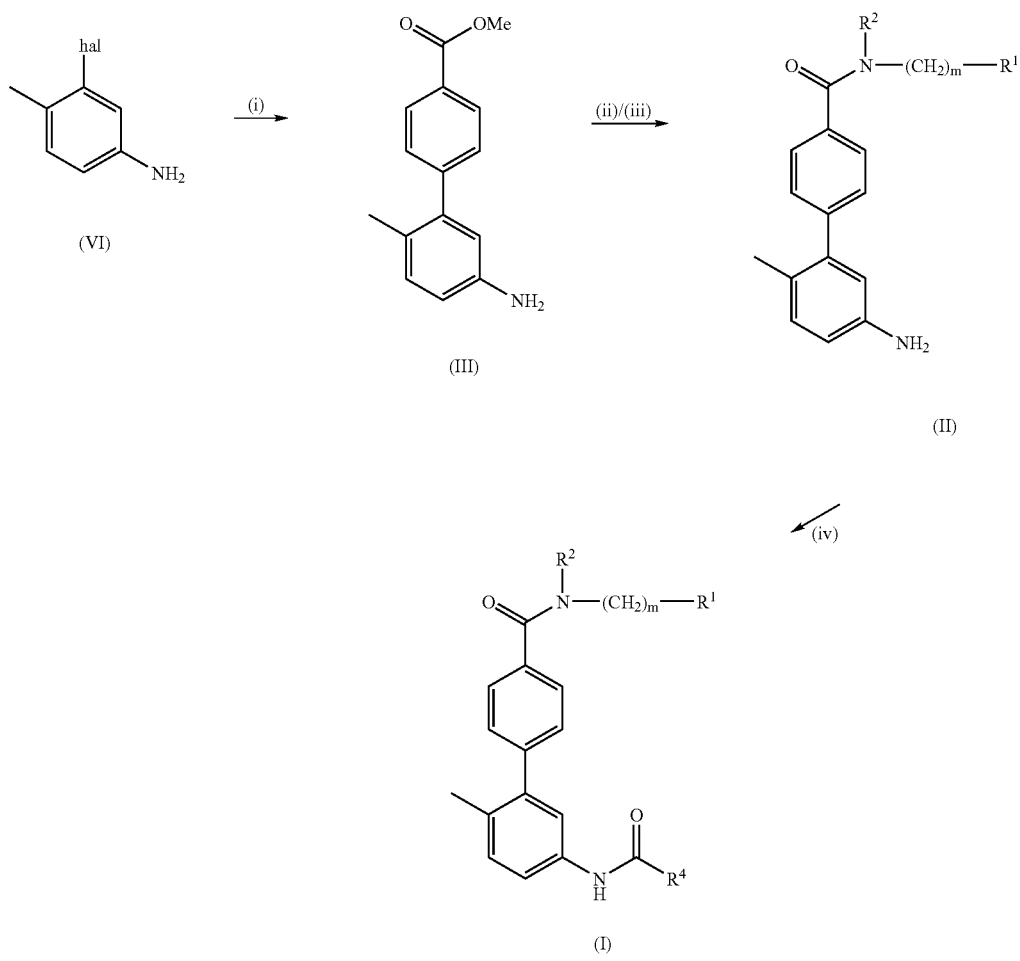

(i) (4-Methoxycarbonylphenyl)boronic acid, (Ph₃P)₄Pd, CsCO₃, DME
(ii) LiOH, THF, H₂O
(iii) R¹(CH₂)ₘN R²H, HATU, DIPEA, THF
(iv) R⁴COCl, Et₃N, DCM Thus, according to the invention there is provided a process for preparing a compound of formula (I) which comprises:
(a) reacting a compound of formula (XI)

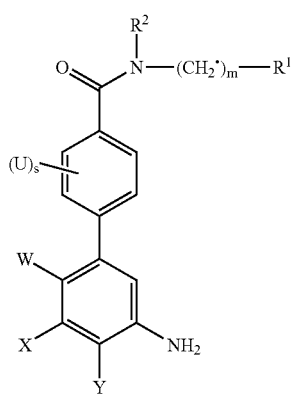

wherein $R^1, R^2, U, W, X, Y, m$ and $s$ are as defined above, with a compound of formula (XII)

R⁶CO₂H        (XII)

wherein $R^6$ is as defined above,
under amide forming conditions (if desired, the acid compound (XII) may be converted to an activated form of the acid, for example the acid chloride, and then the activated acid thus formed reacted with the amine compound (XI); or
(b) reacting a compound of formula (XIII)

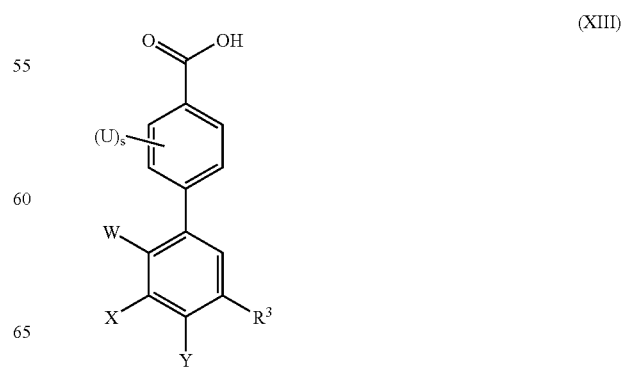

wherein $R^3$, U, W, X, Y and s are as defined above, with a compound of formula (XIV)

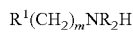 $$R^1(CH_2)_mNR_2H \qquad (XIV)$$

wherein $R^1$, $R^2$ and m are as defined above, under amide forming conditions.

Suitable amide forming conditions are well known in the art and include treating a solution of the acid, in for example THF, with an amine in the presence of, for example, HATU and DIPEA.

Whilst it is possible for the compounds, salts or solvates of the present invention to be administered as the new chemical, the compounds of formula (I) and their pharmaceutically acceptable salts and solvates are conveniently administered in the form of pharmaceutical compositions. Thus, in another aspect of the invention, we provide a pharmaceutical composition comprising a compound of formula (I) or a pharmaceutically acceptable salt or solvate thereof, in admixture with one or more pharmaceutically acceptable carriers, diluents or excipients.

The compounds of formula (I) and their pharmaceutically acceptable salts and solvates may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable salts and solvates. A particularly preferred method of administration, and corresponding formulation, is oral administration.

For oral administration, the pharmaceutical composition may take the form of, and be administered as, for example, tablets (including sublingual tablets) and capsules (each including timed release and sustained release formulations), pills, powders, granules, elixirs, tinctures, emulsions, solutions, syrups or suspensions prepared by conventional means with acceptable excipients.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The pharmaceutical compositions generally are administered in an amount effective for treatment or prophylaxis of a specific condition or conditions. Initial dosing in human is accompanied by clinical monitoring of symptoms, such symptoms for the selected condition. In general, the compositions are administered in an amount of active agent of at least about 100 μg/kg body weight. In most cases they will be administered in one or more doses in an amount not in excess of about 20 mg/kg body weight per day. Preferably, in most cases, dose is from about 100 μg/kg to about 5 mg/kg body weight, daily. For administration particularly to mammals, and particularly humans, it is expected that the daily dosage level of the active agent will be from 0.1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the age, weight and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

In another aspect, the present invention provides a compound of formula (I) or a salt or solvate thereof, for use in therapy.

The compounds of the present invention are generally inhibitors of the serine/threonine kinase p38 and are therefore also inhibitors of cytokine production which is mediated by p38 kinase. Within the meaning of the term "inhibitors of the serine/threonine kinase p38" are included those compounds that interfere with the ability of p38 to transfer a phosphate group from ATP to a protein substrate according to the assay described below.

It will be appreciated that the compounds of the invention may be selective for one or more of the isoforms of p38, for example p38α, p38β, p38γ and/or p38δ. In one embodiment, the compounds of the invention selectively inhibit the p38α isoform. In another embodiment, the compounds of the invention selectively inhibit the p38β isoform. In a further embodiment, the compounds of the invention selectively inhibit the p38α and p38β isoforms. Assays for determining the selectivity of compounds for the p38 isoforms are described in, for example, WO 99/61426, WO 00/71535 and WO 02/46158. It is known that p38 kinase activity can be elevated (locally or throughout the body), p38 kinase can be incorrectly temporally active or expressed, p38 kinase can be expressed or active in an inappropriate location, p38 kinase can be constitutively expressed, or p38 kinase expression can be erratic; similarly, cytokine production mediated by p38 kinase activity can be occurring at inappropriate times, inappropriate locations, or it can occur at detrimentally high levels.

Accordingly, the present invention provides a method for the treatment of a condition or disease state mediated by p38 kinase activity, or mediated by cytokines produced by the activity of p38 kinase, in a subject which comprises administering to said subject a therapeutically effective amount of a compound of formula (I) or a pharmaceutically acceptable salt or solvate thereof. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention also provides a method of inhibiting cytokine production which is mediated by p38 kinase activity in a subject, e.g. a human, which comprises administering to said subject in need of cytokine production inhibition a therapeutic, or cytokine-inhibiting, amount of a compound of the present invention. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms. For example, the clinician can monitor accepted measurement scores for anti-inflammatory treatments.

The compounds of the present invention can be administered to any subject in need of inhibition or regulation of p38 kinase or in need of inhibition or regulation of p38 mediated cytokine production. In particular, the compounds may be administered to mammals. Such mammals can include, for example, horses, cows, sheep, pigs, mice, dogs, cats, primates such as chimpanzees, gorillas, rhesus monkeys, and, most preferably, humans.

Thus, the present invention provides methods of treating or reducing symptoms in a human or animal subject suffering from, for example, rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, hemiated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, cancer including breast cancer, colon cancer, lung cancer or prostatic cancer, which comprises administering to said subject a therapeutically effective amount of a compound of formula(I) or a pharmaceutically acceptable salt or solvate thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy and cancer including breast cancer, colon cancer, lung cancer and prostatic cancer, which comprises administering to said subject a therapeutically effective amount of a compound of formula (I) or a pharmaceutically acceptable salt or solvate thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer, which comprises administering to said subject a therapeutically effective amount of a compound of formula (I) or a pharmaceutically acceptable salt or solvate thereof.

A further aspect of the invention provides a method of treatment of a human or animal subject suffering from rheumatoid arthritis, neurodegenerative disease, Alzheimer's disease, Parkinson's disease and epilepsy which comprises administering to said subject a therapeutically effective amount of a compound of formula (I) or a pharmaceutically acceptable salt or solvate thereof.

A further aspect of the invention provides a method of treatment of a human or animal subject suffering from any type of pain including chronic pain, rapid onset of analgesis, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain which comprises administering to said subject a therapeutically effective amount of a compound of formula (I) or a pharmaceutically acceptable salt or solvate thereof.

A further aspect of the invention provides the use of a compound of formula (I), or a pharmaceutically acceptable salt or solvate thereof, for the preparation of a medicament for the treatment of a condition or disease state mediated by p38 kinase activity or mediated by cytokines produced by p38 kinase activity.

A further aspect of the invention provides the use of a compound of formula (I), or a pharmaceutically acceptable salt or solvate thereof, for the preparation of a medicament for the treatment of a condition or disease state selected from rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, and cancer including breast cancer, colon cancer, lung cancer or prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy, and cancer including breast cancer, colon cancer, lung cancer and prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, neurodegenerative disease, Alzheimer's disease, Parkinson's disease and epilepsy.

A further aspect of the invention provides the use of a compound of formula (I), or a pharmaceutically acceptable salt or solvate thereof, for the preparation of a medicament for the treatment of any type of pain including chronic pain, rapid onset of analgesis, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain.

The compounds of formula (I) and their salts, solvates and physiologically functional salts and solvates may be employed alone or in combination with other therapeutic agents for the treatment of the above-mentioned conditions. In particular, in rheumatoid arthritis therapy, combination with other chemotherapeutic or antibody agents is envisaged. Combination therapies according to the present invention thus comprise the administration of at least one compound of formula (I) or a pharmaceutically acceptable salt or solvate thereof and at least one other pharmaceutically active agent. The compound(s) of formula (I) or pharmaceutically acceptable salt(s) or solvate(s) thereof and the other pharmaceutically active agent(s) may be administered together or separately and, when administered separately, this may occur separately or sequentially in any order. The amounts of the compound(s) of formula (I) or pharmaceutically acceptable salt(s) or solvate(s) thereof and the other pharmaceutically active agent(s) and the relative timings of administration will be selected in order to achieve the desired combined therapeutic effect. Examples of other pharmaceutically active agents which may be employed in combination with compounds of formula (I) and their salts and solvates for rheumatoid arthritis therapy include: immunosuppresants such as amtolmetin guacil, mizoribine and rimexolone; anti-TNFα agents such as etanercept, infliximab, diacerein; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

EXAMPLES

The following examples are illustrative embodiments of the invention, not limiting the scope of the invention in any way. Reagents are commercially available or are prepared according to procedures in the literature. LCMS was conducted on a column (3.3 cm×4.6 mm ID, 3 um ABZ+PLUS), at a Flow Rate of 3 ml/min, Injection Volume of 5 µl, at room temperature and UV Detection Range at 215 to 330 nm.

General Method A

A solution of the 2-chloropyridine (0.17 mmol) in amine (1 ml) was heated at 850° C. for 16 h. The reaction was concentrated under vacuum and the residue purified by SPE (C18, 10 g), eluting with a water, acetonitrile and THF. The solvent was evaporated under vacuum to give the 2-amiriopyridine.

General Method B

Carboxylic acid (0.4 mmol), HATU (0.2 mmol), DIPEA (105 µl), and amine (0.17 mmol) were mixed in DMF (10 ml) and heated for 18 h at 80° C. The solvent was evaporated from the cooled reaction under vacuum and the residue was purified by SPE (silica, 10 g) eluting with DCM and then DCMI ethanol/ammonia (300:8:1 to 100:8:1). The solvent was evaporated under vacuum from the product fractions which were further purified by SPE (C18, 5 g), eluting with water, water/acetonitrile (1:1) and acetonitrile. Evaporation of the solvents under vacuum gave the amide.

General Method C

A solution of the 2-chloropyridine (0.12 mmol) in amine (1 ml) was heated at 85° C. for 96 h in a sealed tube. The reaction was concentrated under vacuum and the residue purified by preparative HPLC. The solvent was evaporated under vacuum to give the 2-aminopyridine.

General Method D

Aniline (0.189 mmol) and carboxylic acid (0.378 mmol) were mixed in DMF (6 ml) and the mixture shaken in a varian tube for 15 min at room temperature. Carbodiimde resin (500 mg) was added and shaking continued for 18 h. The solution was filtered off and the resin washed with DMF (×3). The combined filtrate and washings were filtered through an SCX SPE and the solvent evaporated under vacuum to give the amide.

Example 1

N-(4'-{[(Cyclopropylmethyl)amino]carbonyl}-6-methyl-1,1'-biphenyl-3-yl)nicotinamide a) N-(4'-{[(Cyclopropylmethyl)amino]carbonyl}-6-methyl-1,1'-biphenyl-3-yl)nicotinamide was prepared from 5'-amino-N-(cyclopropylmethyl)-2'-methyl-1,1'-biphenyl-4-carboxamide and nicotinic acid using method B. NMR; δH CDCl$_3$ 9.11,(1H, s), 8.77,(1H, dd), 8.22,(1H, d), 8.11,(1H, s), 7.81,(2H, d), 7.63,(1H, d), 7.46-7.42, (2H, m), 7.38,(2H, d), 7.29,(1H, d), 6.28,(1H, t), 3.31,(2H, m), 2.23,(3H, s), 1.06,(1H, m), 0.56,(2H, m), 0.27,(2H, m). LCMS: retention time 3.18 min, MH$^+$386.

b) 5'-Amino-N-(cyclopropylmethyl)-2'-methyl-1,1'-biphenyl4-carboxamide 5'-(t-Butoxycarbonylamino)-N-(cyclopropylmethyl)-2'-methyl-1,1'-biphenyl-4-carboxamide (1.15 g, 3.02 mmol)was added to a mixture of DCM (5 ml) and trifluoroacetic acid (5 ml) and stirred at room temperature for 18 h. The solvents were evaporated under vacuum and the residue partitioned between DCM (100 ml) and aqueous sodium hydroxide (2N, 50 ml). The organic phase was dried (magnesium sulphate) and concentrated to dryness under vacuum to give 5'-amino-N-(cyclopropylmethyl)-2'-methyl-1,1'-biphenyl-4-carboxamide (0.65 g, 77%). LCMS: retention time 2.77 min, MH$^+$281.

c) 5'-(t-Butoxycarbonylamino)-N-(cyclopropylmethyl)-2'-methyl-1,1'-biphenyl-4-carboxamide 5'-(t-Butoxycarbonylamino)-2'-methyl-1,1'-biphenyl-4-carboxylic acid (1.1 g, 3.36 mmol), cyclopropylmethylamine (262 mg, 3.70 mmol), DIPEA (1.8 ml, 10.1 mmol) and HATU (1.4 g, 3.70 mmol) were stirred in THF (25 ml) at room temperature for 18 h. The reaction was concentrated to dryness under vacuum, the residue dissolved in ethyl acetate (700 ml), washed with hydrochloric acid (2M, 100 ml), aqueous sodium hydroxide (2M, 100 ml) and brine (50 ml). The organic phase was dried (magnesium sulphate) and the solvent evaporated under vacuum. The residue was dissolved in ethyl acetate and filtered through SPE (silica, 2×10 g) washing with further ethyl acetate. Concentration of the product fractions under vacuum gave 5'-(t-butoxycarbonylamino)-N-(cyclopropylmethyl)-2'-methyl-1,1'-biphenyl-4-carboxamide (1.15 g, 90%). LCMS: retention time 3.71 min, MH$^+$381.

d) 5'-(t-Butoxycarbonylamino)-2'-methyl-1,1'-biphenyl-4-carboxylic acid Methyl 5'-(t-butoxycarbonylamino)-2'-methyl-1,1'-biphenyl-4-carboxylate (2.32 g, 6.8 mmol) and aqueous sodium hydroxide (2N, 7 ml) were refluxed in methanol (40 ml) for 12 h. The solution was filtered through a celite pad and the filtrate concentrated to dryness under vacuum. The residue was dissolved in ethyl acetate, washed with hydrochloric acid (2M, 100 ml), dried (magnesium sulphate) and concentrated to dryness under vacuum to give 5'-(t-butoxycarbonylamino)-2'-methyl-1,1'-biphenyl-4-carboxylic acid (1.1 g, 49%). LCMS: retention time 3.77 min, MH$^+$328.

e) Methyl 5'-(t-butoxycarbonylamino)-2'-methyl-1,1'-biphenyl-4-carboxylate (4-Methoxycarbonylphenyl)boronic acid (1.51 g, 8.4 mmol), t-butyl-N-(3-bromo-4-methylphenyl)carbamate (2.0 g, 6.99 mmol), caesium carbonate (2.7 g, 8.4 mmol) and tetrakis(triphenylphosphine)palladium (0.8 g, 0.69 mmol) were heated at reflux in degassed DME (40 ml) for 18 h. The reaction was filtered through a celite pad washing with DME. The combined filtrate and washings were absorbed onto silica and chromatographed on a silica gel flash column eluting with ethyl acetate/cyclohexane (1:3). Evaporation of the solvent from the product fractions under vacuum gave methyl 5'-(t-butoxycarbonylamino)-2'-methyl-1,1'-biphenyl-4-carboxylate (2.32 g, 97%). NMR; δH CDCl$_3$ 8.07,(2H, d), 7.39,(2H, d), 7.28,(1H, b), 7.24,(1H, b), 7.19,(1H, d), 3.94,(3H, s), 2.19,(3H, s), 1.51,(9H, s). LCMS: retention time 3.93 min.

f) t-Butyl-N-(3-bromo-4-methylphenyl)carbamate Di-tert-butyl dicarbonate (5.45 g, 0.025 mmol) was added to a solution of 3-bromo-4-methylaniline (4.65 g, 0.025 mmol) and triethylamine (3.85 ml, 0.028 mmol) in DCM (50 ml), and the mixture stirred at room temperature for 48 h. The reaction was diluted with DCM (100 ml), washed with hydrochloric acid (2N, 100 ml), water (100 ml), brine and dried (sodium sulphate). The organic phase was absorbed onto silica and flash chromatographed on a silica gel column eluting with ethyl acetate/ cyclohexane (1:3) to give, after evaporation of the solvents under vacuum, t-butyl —N-(3-bromo-4-methylphenyl)carbamate (4.5 g, 63%). NMR; •H CDCl$_3$ 7.65,(1H, s), 7.12,(2H, m), 6.41,(1H, b), 2.33,(3H, s), 1.51 ,(9H, s).

Example 2

4-Chloro-N-(4'-{[(cyclopropylmethyl)amino]carbonyl}-6-methyl-1,1'-biphenyl-3-yl)benzamide 4-Chloro-N-(4'-{[(cyclopropylmethyl)amino]carbonyl}-6-methyl-1,1'-biphenyl-3-yl)benzamide was prepared from 5'-amino-N-(cyclopropylmethyl)-2'-methyl-1,1'-biphenyl-4-carboxamide and 4-chlorobenzoic acid using method B. LCMS: retention time 3.73 min, MH$^+$419.

Example 3

N-(4'-{[(Cyclopropylmethyl)amino]carbonyl}-6-methyl-1,1'-biphenyl-3-yl)-4-methylbenzamide N-(4'-{[(Cyclopropylmethyl)amino]carbonyl}-6-methyl-1,1'-biphenyl-3-yl)-4-methylbenzamide was prepared from 5'-amino-N-(cyclopropylmethyl)-2'-methyl-1,1'-biphenyl-4-carboxamide and 4-methylbenzoic acid using method B. NMR; $^{TM}$H CDCl$_3$ 7.87,(1H, s), 7.83,(2H, d), 7.78,(2H, d), 7.60,(1H, dd), 7.49,(1H, d), 7.41,(2H, d), 7.29-7.26,(3H, m), 6.29,(1H, t), 3.35,(2H, m), 2.42,(3H, s), 2.23,(3H, s), 1.09, (1H, m), 0.58,(2H, m), 0.30,(2H, m). LCMS: retention time 3.63 min, MH$^+$399.

Example 4

2-Amino-N-(4'-{[(cyclopropylmethyl)amino]carbonyl}-6-methyl-1,1'-biphenyl-3-yl)isonicotinamide 2-Amino-N-(4'-{[(cyclopropylmethyl)amino]carbonyl}-6-methyl-1,1'-biphenyl-3-yl)isonicotinamide was prepared from 5'-amino-N-(cyclopropylmethyl)-2'-methyl-1,1'-biphenyl-4-carboxamide and 2-aminoisonicotinic acid using method B. NMR; δH CDCl$_3$ 8.20,(1H, d), 7.93,(1H, s), 7.82, (2H, d), 7.60,(1H, d), 7.46,(1H, s), 7.39,(2H,d), 7.30-7.26, (2H, m), 6.96,(1H, s), 6.29,(1H, b), 4.67,(2H, s), 3.34,(2H, m), 2.24,(3H, s), 1.08,(1H, m), 0.59,(2H, m), 0.30,(2H, m). LCMS: retention time 2.75 min, MH$^+$401.

Example 5

N-(4'-{[(Cyclopropylmethyl)amino]carbonyl}-6-methyl-1,1'-biphenyl-3-yl-3-furamide N-(4'-{[(Cyclopropylmethyl)amino]carbonyl}-6-methyl-1,1'-biphenyl-3-yl)-3-furamide was prepared from 5'-amino-N-(cyclopropylmethyl)-2'-methyl-1,1'-biphenyl-4-carboxamide and 3-furoic acid using method B. NMR; δH CDCl$_3$ 8.10,(1H, s), 7.97,(1H, s), 7.78,(2H, d), 7.64,(1H, dd), 7.47, (1H, m), 7.38,(1H, d), 7.33,(2H, d), 7.24,(1H, d), 6.80,(1H, s), 6.36,(1H, t), 3.32,(2H, m), 2.21,(3H, s), 1.06,(1H, m), 0.57, (2H, m), 0.28,(2m). LCMS: retention time 3.38 min, MH$^+$375.

Example 6

2-Chloro-N-(4'-{[(cyclopropylmethyl)amino]carbonyl}-6-methyl-1,1'-biphenyl-3-yl)isonicotinamide 5-Amino-N-(cyclopropylmethyl)-2'-methyl-1,1'-biphenyl-4-carboxamide (260 mg, 0.93 mmol), 2-chloropyridine-4-carbonyl chloride (245 μl) and triethylamine (195 μl, 1.39 mmol) were stirred at room temperature in DCM (20 ml) for 72 h. The reaction was diluted with DCM (100 ml), washed with aqueous sodium hydroxide (2M, 100 ml) and dried (magnesium sulphate). The solvent was evaporated under vacuum, the residue dissolved in methanol and purified by SPE (C18, 10 g) eluting with water, water/acetonitrile (1:1) and acetonitrile. The solvent was evaporated from the product fractions under vacuum to give 2-chloro-N-(4'-{[(cyclopropylmethyl)amino]carbonyl}-6-methyl-1,1'-biphenyl-3-yl)isonicotinamide (130 mg, 33%). NMR; δH [$^2$H$_6$]—DMSO 10.57,(1H, s), 8.63-8.60,(2H, m), 7.99,(1H, s), 7.93,(2H, d), 7.86,(1H, dd),7.70,(1H, dd), 7.66,(1H, d), 7.44,(2H, d), 7.32, (1H, d), 3.16,(2H, t), 2.21,(3H, s), 1.05,(1H, m), 0.43,(2H, m), 0.24,(2H, m). LCMS: retention time 3.53 min, MH$^+$420/422.

Example 7

N-(4'-{[(CycloPropylmethyl)amino]carbonyl}-6-methyl-1,1'-biphenyl-3-yl)-2-Piperidin-1-ylquinoline-4-carboxamide N-(4'-{[(Cyclopropylmethyl)amino]carbonyl}-6-methyl-1,1'-biphenyl-3-yl)-2-piperidin-1-ylquinoline-4-carboxamide was prepared from 5'-amino-N-(cyclopropylmethyl)-2'-methyl-1, 1'-biphenyl-4-carboxamide and 2-(piperidin-1-yl)quinoline-4-carboxylic acid using method B. NMR; δH CDCl$_3$ 7.90,(1H, d), 7.83-7.78,(4H, m), 7.67,(1H, b), 7.52, (1H, t), 7.42,(2H, d), 7.33,(1H, d), 7.26, (1H, m), 7.21,(1H, t), 7.01,(1H, s), 6.30,(1H, t), 3.63,(4H, s), 3.31,(2H, m), 2.27, (3H, s), 1.62,(6H, m), 1.07,(1H, m), 0.57,(2H, m), 0.28,(2H, m). LCMS: retention time 3.32 min, MH$^+$519.

Example 8

N-(4'-{[(Cyclopropylmethyl)amino]carbonyl}-6-methyl-1,1'-biphenyl-3-yl)-2-Pyrrolidin-1-ylisonicotinamide N-(4'-{[(Cyclopropylmethyl)amino]carbonyl}-6-methyl-1,1'-biphenyl-3-yl)-2-pyrrolidin-1- ylisonicotinamide was prepared from 2-chloro-N-(4'-{[(cyclopropylmethyl)amino]carbonyl}-6-methyl-1,1'-biphenyl-3-yl)isonicotinamide and pyrrolidine using method A. NMR; δH [$^2$H$_6$]—DMSO 10.28, (1H. s), 8.62,(1H, t), 8.19,(1H, d), 7.93,(2H, d), 7.71,(1H, dd), 7.66,(1H, d), 7.44,(2H, d), 7.30,(1H, d), 6.97,(1H, d), 6.86, (1H, s), 3.43,(4H, m), 3.16,(2H, t), 2.20,(3H, s), 1.95,(4H, m), 1.04,(1H, b), 0.43,(2H, m), 0.24,(2H, m). LCMS: retention time 2.85 min, M$^+$455.

Example 9

N-(4'-{[(Cyclopropylmethyl)amino]carbonyl}-6-methyl-1,1'-biphenyl-3-yl)-2-(4-methylpiperazin-1-yl)isonicotinamide N-(4'-{[(Cyclopropylmethyl)amino]carbonyl}-6-methyl-1,1'-biphenyl-3-yl)-2-(4-methylpiperazin-1-yl)isonicotinamide was prepared from 2-chloro-N-(4'-{[(cyclopropylmethyl)amino]carbonyl}-6-methyl-1,1'-biphenyl-3yl)isonicotinamide and N-methylpiperazine using method A. NMR; δH [$^2$H$_6$]—DMSO 10.31,(1H, s), 8.62,(1H, t), 8.24, (1H, d), 7.93,(2H, d), 7.71,(1H, dd), 7.64,(1H, d), 7.44,(2H, d), 7.30,(1H, d), 7.23,(1H, s), 7.06,(1H, d), 3.55,(4H, m), 3.16,(2H, t), 2.40,(4H, t), 2.21,(6H, m), 1.04,(1H, m), 0.43, (2H, m), 0.24,(2H, m). LCMS: retention time 2.74 min, MH$^+$484.

Example 10

N-(4'-{[(Cyclopropylmethyl)amino]carbonyl}-6-methyl-1,1'-biphenyl-3-yl)-2-morpholin-4-ylisonicotinamide N-(4'-{[(Cyclopropylmethyl)amino]carbonyl}-6-methyl-1,1'-biphenyl-3-yl)-2-morpholin-4- ylisonicotinamide was prepared from 2-chloro-N-(4'-{[(cyclopropylmethyl)amino]carbonyl}-6-methyl-1,1'-biphenyl-3-yl)isonicotinamide and morpholine using method A. NMR; δH [$^2$H$_6$]—DMSO 10.32,(1H, s), 8.62,(1H, t), 8.27,(1H, d), 7.93,(2H, d), 7.70, (1H, dd), 7.64,(1H, d), 7.44,(2H, d), 7.30,(1H, d), 7.24,(1H, s), 7.11,(1H, d), 3.71,(4H, m), 3.51,(4H, m), 3.16,(2H, t), 2.20,(3H, s), 1.05,(1H, m), 0.43,(2H, m), 0.24,(2H, m). LCMS: retention time 3.31 min, MH$^+$471.

Example 11

N-(4'-{[(Cyclopropylmethyl)amino]carbonyl}-6-methyl-1,1'-biphenyl-3-yl)-2-Piperidin-1-ylisonicotinamide N-(4'-{[(Cyclopropylmethyl)amino]carbonyl}-6-methyl-1,1'-biphenyl-3-yl)-2-piperidin-1- ylisonicotinamide was prepared from 2-chloro-N-(4'-{[(cyclopropylmethyl)amino]carbonyl}-6-methyl-1,1'-biphenyl-3-yl)isonicotinamide and piperidine using method A. NMR; δH [$^2$H$_6$]—DMSO 10.29, (1H,s), 8.62,(1H, t), 8.22,(1H, d), 7.93,(2H, d), 7.71,(1H, dd), 7.65,(1H, d), 7.44,(2H, d), 7.30,(1H, d), 7.20,(1H, s), 6.99, (1H, d), 3.58,(4H, m), 3.16,(2H, t), 2.20,(3H, s), 1.60-1.54, (6H, m), 1.04,(1H, m), 0.43,(2H, m), 0.24,(2H, m). LCMS: retention time 3.43 min, MH$^+$469.

Example 12

N-(4'-{[(Cyclopropylmethyl)amino]carbonyl}-6-methyl-1,1'-biphenyl-3-yl)-2-dimethylaminoisonicotinamide 2-Chloro-N-(4'-{[(cyclopropylmethyl)amino]carbonyl}-6-methyl-1,1'-biphenyl-3-yl)isonicotinamide and dimethylamine (40% in water) in DMF (1 ml) were heated at 85° C. for 96 h in a sealed tube. The reaction mixture was concentrated under vacuum, purified by preparative HPLC and the product fractions reduced to dryness under vacuum to give N-(4'-{[(cyclopropylmethyl)amino]carbonyl}-6-methyl-1, 1'-biphenyl-3-yl)-2-(dimethylamino)isonicotinamide. NMR; δH [$^2$H$_6$]—DMSO 10.29,(1H, s), 8.62,(1H, t), 8.22,(1H, d), 7.93,(2H, d), 7.70,(1H, dd), 7.65,(1H, d), 7.44,(2H, d), 7.30, (1H, d), 7.03,(1H, s), 6.99,(1H, d), 3.16,(2H, t), 3.07,(6H, s), 2.20,(3H, s), 1.04,(1H, m), 0.43,(2H, m), 0.24,(2H, m). LCMS: retention time 2.88 min, MH$^+$429.

Example 13

2-(Cyclopropylmethylamino)-N-4'-{[(cyclopropylmethyl)amino]carbonyl}-6-methyl-1,1'-biphenyl-3-yl)isonicotinamide A solution of 2-chloro-N-(4'-{[(cyclopropylmethyl)amino]carbonyl}-6-methyl-1,1'-biphenyl-3-yl)isonicotinamide (50 mg, 0.12 mmol) in cyclopropylmethylamine (1 ml) was heated at 85° C. for 48 h and then at 110° C. for 48 h in a sealed tube. The reaction was concentrated under vacuum, the residue triturated with water and purified by preparative HPLC. The solvent was evaporated under vacuum to give 2-(cyclopropylmethylamino)-N-(4'-{[(cyclopropylmethyl)amino]carbonyl}-6-methyl-1,1'-biphenyl-3-yl)isonicotinamide (17.1 mg, 32%). NMR; $\epsilon$H [$^2$H$_6$]—DMSO 10.27,(1H, s), 8.62,(1H, t), 8.08,(1H, d), 7.93,(2H, d), 7.70-7.66,(2H, m), 7.44,(2H, d), 7.28,(1H, d), 6.89-6.87,(3H, m), 3.16,(4H, m), 2.20,(3H, s), 1.04,(2H, m), 0.43,(4H, m), 0.25-0.19,(4H, m). LCMS: retention time 2.96 min, MH$^+$455.

Example 14

N-(4'-{[(Cyclopropylmethyl)amino]carbonyl}-6-methyl-1,1'-biphenyl-3-yl)-2-(isobutylamino)isonicotinamide N-(4'-{[(Cyclopropylmethyl)amino]carbonyl}-6-methyl-1,1'-biphenyl-3-yl)-2-(isobutylamino)isonicotinamide was prepared from 2-chloro-N-(4'-{[(cyclopropylmethyl)amino]carbonyl}-6-methyl-1,1'-biphenyl-3-yl)isonicotinamide and isobutylamine using method C. NMR; δH [$^2$H$_6$]-DMSO 10.27,(1H, s), 8.62,(1H, t), 8.07,(1H, d), 7.93,(2H, d), 7.70-7.66,(2H, m), 7.43,(2H, d), 7.28,(1H, d), 6.88-6.84,(3H, m), 3.16,(2H, t), 3.09,(2H, t), 2.20,(3H, s), 1.83,(1H, m), 1.04, (1H, m), 0.90,(6H, d), 0.43,(2H, m), 0.24,(2H, m). LCMS: retention time 3.02 min, MH$^+$457.

Example 15

N-(4'-{[(Cyclopropylmethyl)amino]carbonyl}-6-methyl-1,1'-biphenyl-3-yl)-2-thiomorpholin-4-yl-isonicotinamide A solution of 2-chloro-N-(4'-{[(cyclopropylmethyl)amino]carbonyl}-6-methyl-1,1'-biphenyl-3-yl)isonicotinamide (50 mg, 0.12 mmol) in thiomorpholine (1 ml) was heated at 110° C. for 36 h in a sealed tube. The reaction was concentrated under vacuum, the residue triturated with water and purified by preparative HPLC. The solvent was evaporated under vacuum to give N-(4'-{[(cyclopropylmethyl)amino]carbonyl}-6-methyl-1,1'-biphenyl-3-yl)-2-thiomorpholin-4-ylisonicotinamide (25 mg). NMR; δH [$^2$H$_6$]—DMSO 10.30,(1H, s), 8.62,(1H, t), 8.25,(1H, d), 7.93,(2H, d), 7.70,(1H, dd), 7.64,(1H, d), 7.44,(2H, d), 7.30,(1H, d), 7.22, (1H, s), 7.03,(1H, d), 3.96,(4H, m), 3.16,(2H, t), 2.62,(4H, m), 2.20,(3H, s), 1.05,(1H, m), 0.43,(2H, m), 0.24,(2H, m). LCMS: retention time 3.57 min, MH$^+$487.

Example 16

2-(Cyclohexylamino)-N-(4'-{[(cyclopropylmethyl)amino]carbonyl}-6-methyl-1,1'-biphenyl-3-yl)isonicotinamide A solution of 2-chloro-N-(4'-{[(cyclopropylmethyl)amino]carbonyl}-6-methyl-1,1'-biphenyl-3-yl)isonicotinamide (50 mg, 0.12 mmol) in cyclohexylamine (1 ml) was heated at 110° C. for 36 h and then at 160° C. for 48 h in a sealed tube. The reaction was concentrated under vacuum, the residue triturated with water and purified by preparative HPLC. The solvent was evaporated under vacuum to give 2-cyclohexylamino)-N-(4'-{[(cyclopropylmethyl)amino]carbonyl}-6-methyl-1,1'-biphenyl-3-yl)isonicotinamide (14.4 mg). NMR; δH [$^2$H$_6$]—DMSO 10.26,(1H, s), 8.62,(1H, t), 8.07,(1H, d), 7.92,(2H, d), 7.69-7.66,(2H, m), 7.43,(2H, d), 7.28,(1H, d), 6.84,(2H, m), 6.67,(1H, d), 3.72,(1H, m), 3.16, (2H, t), 2.19,(3H, s), 1.90,(2H, m), 1.70,(2H, m), 1.57,(1H, m), 1.31,(2H, m), 1.18,(3H, m), 1.04,(1H, m), 0.24,(2h, m). LCMS: retention time 3.14 min, MH$^+$483.

Example 17

2-(Cyclopropylamino)-N-(4'-{[(cyclopropylmethyl)amino]carbonyl}-6-methyl-1,1'-biphenyl-3-yl)isonicotinamide A solution of 2-chloro-N-(4'{[(cyclopropylmethyl)amino]carbonyl}-6-methyl-1,1'-biphenyl-3-yl)isonicotinamide (50 mg, 0.12 mmol) in cyclopropylamine (2 ml) was heated at 85° C. for 48 h and then at 110° C. for 72 h in a sealed tube.The reaction was concentrated under vacuum, the residue triturated with water and purified by preparative HPLC. The solvent was evaporated under vacuum to give 2-(cyclopropylamino)-N-4'-{[(cyclopropylmethyl)amino]carbonyl}-6-methyl-1,1'-biphenyl-3-yl)isonicotinamide (6 mg). NMR; δH [$^2$H$_6$]—DMSO 10.32,(1H, s), 8.62,(1H, t), 8.14,(1H, d), 7.93,(2H, d), 7.71-7.67,(2H, m), 7.44,(2H, d), 7.29,(1H, d), 7.05,(1H, d), 7.00-6.98,(2H, m), 3.16,(2H, t), 2.55,(1H, m), 2.20,(3H, s), 1.05,(1H, m), 0.71,(2H, m), 0.43,(4H, m), 0.24, (2H, m). LCMS: retention time 2.74 min, MH$^+$441.

Example 18

N-(4'-{[(Cyclopropylmethyl)amino]carbonyl}-6-methyl-1,1'-biphenyl-3-yl)-2-(diethylamino)isonicotinamide A solution of 2-chloro-N-(4'-{[(cyclopropylmethyl)amino]carbonyl}-6-methyl-1,1'-biphenyl-3-yl)isonicotinamide (50 mg, 0.12 mmol) in diethylamine (2 ml) was heated at 80° C. for 48 h and then at 110° C. for 84 h in a sealed tube. The reaction was concentrated under vacuum, the residue triturated with water and purified by preparative HPLC. The solvent was evaporated under vacuum to give N-(4'-{[(cyclopropylmethyl)amino]carbonyl}-6-methyl-1,1'-biphenyl-3-yl)-2-diethylamino)isonicotinamide. NMR; δH [$^2$H$_6$]—DMSO 10.27,(1H, s), 8.62,(1H, t), 8.19,(1H, d), 7.93,(2H, d), 7.69,(1H, dd), 7.65,(1H, d), 7.44,(2H, d), 7.30,(1H, d), 0.43, (4H, m), 0.24,(2H, m). LCMS: retention time 3.09 min, MH$^+$457.

Example 19

N-(4'-{[(Cyclopropylmethyl)amino]carbonyl}-6-methyl-1,1'-biphenyl-3-yl)-2-(4-methylriperidin-1-yl)isonicotinamide A solution of 2-chloro-N-(4'-{[(cyclopropylmethyl)amino]carbonyl}-6-methyl-1,1'-biphenyl-3-yl)isonicotinamide (50 mg, 0.12 mmol) in 4-methylpiperidine (1 ml) was heated at 120° C. for 18 h in a sealed tube. The reaction was concentrated under vacuum, the residue triturated with water to give N-(4'-{[(cyclopropylmethyl)amino]carbonyl}-6-methyl-1,1'-biphenyl-3-yl)-2-(4-methylpiperidin-1-yl)isonicotinamide (39 mg). NMR; δH [$^2$H$_6$]—DMSO 10.28,(1H, s), 8.62,(1H, t), 8.22,(1$_1$, d), 7.93,(2H, d), 7.71,(1H, d), 7.64,(1H, s), 7.44,(2H, d), 7.30,(1H, d), 7.21,(1H, s), 7.00,(1H, d), 4.35,(2H, m), 3.16,(2H, t), 2.83,(2H, m), 2.20,(3H, s), 1.69-1.60,(3H, m), 1.07,(3H, m), 0.92,(3H, d), 0.43,(2H, m), 0.24, (2H, m). LCMS: retention time 3.55 min, MH$^+$483.

Example 20

N-(4'-{[(Cyclopropylmethyl)amino]carbonyl}-6-methyl-1,1'-biphenyl-3-yl)-2-(2-methylpyrrolidin-1-yl)isonicotinamide A solution of 2-chloro-N-(4'-{[(cyclopropylmethyl)amino]carbonyl}-6-methyl-1,1'-biphenyl-3-yl)isonicotinamide (50 mg, 0.12 mmol) in 2-methylpyrrolidine (1 ml) was heated at 120° C. for 18 h in a sealed tube. The reaction was concentrated under vacuum, the residue triturated with water to give N-(4'-{[(cyclopropylmethyl)amino]carbonyl}-6-methyl-1,1'-biphenyl-3-yl)-2-(2-methylpyrrolidin-1-yl)isonicotinamide (35 mg). NMR; δH [$^2$H$_6$]—DMSO 10.27,(1H, s), 8.62,(1H, t), 8.20,(1H, d), 7.93,(2H, d), 7.70,(1H, d), 7.66, (1H, s), 7.44,(2H, d), 7.30,(1H, d), LCMS: retention time 2.89 min, MH$^+$469.

Example 21

N-(4'-{[(Cyclopropylmethyl)amino]carbonyl}-6-methyl-1,1'-biphenyl-3-yl)-2-(3-dimethylaminopyrrolidin-1-yl)isonicotinamide A solution of 2-chloro-N-(4'-{[(cyclopropylmethyl)amino]carbonyl}-6-methyl-1,1'-biphenyl-3-yl)isonicotinamide (50 mg, 0.12 mmol) in 3(dimethylamino)pyrrolidine (1 ml) was heated at 120° C. for 18 h in a sealed tube. The reaction was concentrated under vacuum, the residue triturated with water to give N-(4'-{[(cyclopropylmethyl)amino]carbonyl}-6-methyl-1,1'-biphenyl-3-yl)-2-(3-dimethylaminopyrrolidin-1-yl)isonicotinamide (38 mg). NMR; δH [$^2$H$_6$]—DMSO includes 10.28,(1H, s), 8.62,(1H, t), 8.20, (1H, d), 7.93,(2H, d), 7.71,(1H, dd), 7.65,(1H, d), 7.44,(2H, d), 7.30,(1H, d), 6.98,(1H, d), 6.87,(1H, s), 3.72,(1H, m), 3.62,(1H, m), 3.37,(1H, m), 3.16,(3H, m), 2.80,(1H, b), 2.21, (9H, m), 1.81,(1H, m), 1.04,(1H, m), 0.43,(2H, m), 0.24,(2H, m). LCMS: retention time 2.55 min, MH$^+$498.

Example 22

N-(4'-{[(Cyclopropylmethyl)amino]carbonyl}-6-methyl-1,1'-biphenyl-3-yl)-2-(1,2,3,6-tetrahydropyrid-1-yl)isonicotinamide A solution of 2-chloro-N-(4'-{[(cyclopropylmethyl)amino]carbonyl}-6-methyl-1,1'-biphenyl-3-yl)isonicotinamide (50 mg, 0.12 mmol) in 1,2,3,6-tetrahydropyridine (1 ml) was heated at 120° C. for 18 h in a sealed tube. The reaction was concentrated under vacuum, the residue chromatographed on an SPE (C18) eluting with a water/acetonitrile gradient, to give after evaporation of the solvents under vacuum N-(4'-{[(cyclopropylmethyl)amino]carbonyl}-6-methyl-1,1'-biphenyl-3-yl)-2-(1,2,3,6-tetrahydropyrid-1-yl)isonicotinamide. NMR; δH [$^2$H$_6$]—DMSO 10.31,(1H, s), 8.62,(1H, t), 8.25,(1H, d), 7.93,(2H, d), 7.72,(1H, dd), 7.65, (1H, d), 7.44,(2H, d), 7.30,(1H, d), 7.18,(1H, s), 7.04,(1H, d), 5.90,(1H, m), 5.83,(1H, m), 3.99,(2H, m), 3.75,(2H, t), 3.16, (2H, t), 2.21,(5H, m), 1.04,(1H, m), 0.43,(2H, m), 0.24,(2H, m). LCMS: retention time 3.44 min, MH$^+$467.

Example 23

N-(4'-{[(Cyclopropylmethyl)amino]carbonyl}-6-methyl-1,1'-biphenyl-3-yl)-2-(3-methylpiperidin-1-yl)isonicotinamide A solution of 2-chloro-N-(4'-{[(cyclopropylmethyl)amino]carbonyl}-6-methyl-1,1'-biphenyl-3-yl)isonicotinamide (50 mg, 0.12 mmol) in 3-methylpiperidine (1 ml) was heated at 120° C. for 18 h in a sealed tube. The reaction was concentrated under vacuum, the residue chromatographed on an SPE (C18) eluting with a water/acetonitrile gradient, to give, after evaporation of the solvents under vacuum N-(4'-{[(cyclopropylmethyl)amino]carbonyl}-6-methyl-1,1'-biphenyl-3-yl)-2-(3-methylpiperidin-1-yl)isonicotinamide (16 mg). NMR; δH [$^2$H$_6$]—DMSO includes 10.28,(1H, s), 8.62, (1H, t), 8.21,(1H, d), 7.93,(2H, d), 7.70,(1H, dd), 7.65,(1H, d), 7.44,(2H, d), 7.30,(1H, d), 7.20,(1H, s), 6.98,(1H, d), 4.26,(2H, m), 3.16,(2H, t), 2.80,(1H, m), 2.20,(3H, s), 1.78, (1H, m), 1.68,(1H, m), 1.57,(1H, m), 1.45,(1H, m), 1.15,(1H, m), 1.04,(1H, m),0.91,(2H, d), 0.43,(2H, m), 0.24,(2H, m). LCMS: retention time 3.54 min, MH$^+$483.

Example 24

N-(4'-{[(Cyclopropylmethyl)amino]carbonyl}-6-methyl-1,1'-biphenyl-3-yl)-2-(3.5dimethylpiperidin-1-yl)isonicotinamide A solution of 2-chloro-N-(4'-{[(cyclopropylmethyl)amino]carbonyl}-6-methyl-1,1'-biphenyl-3-yl)isonicotinamide (50 mg, 0.12 mmol) in 3,5-dimethylpiperidine (1 ml) was heated at 120° C. for 18 h in a sealed tube. The reaction was concentrated under vacuum, the residue purified by preparative HPLC, to give, after evaporation of the solvents under vacuum N-(4'-{[(cyclopropylmethyl)amino]carbonyl}-6-methyl-1,1'-biphenyl-3-yl)-2-(3,5-dimethylpiperidin-1-yl)isonicotinamide. NMR; δH [$^2$H$_6$] —DMSO 10.29, (1H, s), 8.62,(1H, t), 8.21,(1H, d), 7.93,(2H, d), 7.70,(1H, dd), 7.65,(1H, d), 7.44,(2H, d), 7.30,(1H, d), 7.20,(1H, s), 6.98, (1H, d), 4.35,(2H, m), 3.16,(2H, t), 2.30,(2H, t), 2.20,(3H, s), 1.78,(1H, m), 1.57,(2H, m), 1.04,(1H, m), 0.91,(6H, d), 0.80,(1 H, q), 0.43,(2H, m), 0.24,(2H, m). LCMS: retention time 3.61 min, MH$^+$497.

Example 25

N-(4'-{[(Cyclopropylmethyl)amino]carbonyl}-6-methyl1,1'-biphenyl-3-yl)-2-(2-methoxymethylpyrrolidin-1-yl)isonicotinamide A solution of 2-chloro-N-(4'-{[(cyclopropylmethyl)amino]carbonyl}-6-methyl-1,1'-biphenyl-3-yl)isonicotinamide (50 mg, 0.12 mmol) and 2-(methoxymethyl)pyrrolidine (1 ml) in DMSO (1 ml) was heated at 140° C. for 24 h in a sealed tube. The reaction was concentrated under vacuum, the residue chromatographed on an SPE (C18) eluting with a water/acetonitrile gradient, to give, after evaporation of the solvents under vacuum N-(4'-{[(cyclopropylmethyl)amino]carbonyl}-6-methyl-1,1'-biphenyl-3-yl)-2-(2-methoxymethylpyrrolidin-1-yl)isonicotinamide (16 mg). NMR; δH [$^2$H$_6$]—DMSO 10.29,(1H, s), 8.62,(1H, t), 8.21,(1H, d), 7.93, (2H, d), 7.70,(1H, dd), 7.65,(1H, d), 7.44,(2H, d), 7.30,(1H, d), 7.00,(1H, d), 6.89,(1H, s), 4.23,(1H, b), 3.52-3.47,(2H, m), 3.26,(5H, m), 3.16,(2H, t), 2.20,(3H, s), 2.07-1.90,(4H, m), 1.04,(1H, m), 0.43,(2H, m), 0.24,(2H, m). LCMS: retention time 2.78 min, MH$^+$499.

Example 26

2-(Cyclobutylamino)-N-(4'-{[(cyclopropylmethyl) amino]carbonyl}-6-methyl-1,1'-biphenyl-3-yl)isonicotinamide A solution of 2-chloro-N-(4'-{[(cyclopropylmethyl) amino]carbonyl}-6-methyl-1,1'-biphenyl-3-yl)isonicotinamide (50 mg, 0.12 mmol) and cyclobutylamine (1 ml) in DMSO (1 ml) was heated at 140° C. for 72 h in a sealed tube. The reaction was concentrated under vacuum, the residue purified by preparative HPLC, to give, after evaporation of the solvents under vacuum 2-(cyclobutylamino)-N-(4'-{[(Cyclopropylmethyl)amino]carbonyl}-6-methyl-1,1'-biphenyl-3-yl)isonicotinamide. NMR; δH [$^2$H$_6$]—DMSO 10.27,(1H, s), 8.62,(1H, t), 8.08,(1H, d), 7.93,(2H, d), 7.70-7.65,(2H, m), 7.43,(2H, d), 7.28,(1H, d), 7.06,(1H, d), 6.90,(1H, d), 6.81, (1H, s), 4.30,(1H, m), 3.16,(2H, t), 2.26,(2H, m), 2.20,(3H, s), 1.87,(2H, m), 1.67,(2H, m), 1.04,(1H, m), 0.43,(2H, m), 0.24, (2H, m). LCMS: retention time 2.82 min, MH$^+$455.

Example 27

N-4'-{[(Cyclopropylamino)carbonyl]-6-methyl-1,1'-biphenyl-3-yl}-2-pyrrolidin-1-ylisonicotinamide a) 2'-Methyl-5'-[(2-pyrrolidin-1-ylisonicotinoyl)amino]-1,1'-biphenyl-4-carboxylic acid (40 mg, 0.1 mmol), HATU (38 mg, 0.1 mmol), HOBT (13mg, 0.1 mmol), DIPEA (52 μl), and cyclopropylamine (7 mg, 0.12 mmol) were mixed in DMF (1 ml) and stirred at room temperature for 18 h. The solvent was evaporated under vacuum and the residue partitioned between DCM (5 ml) and aqueous sodium carbonate (1M, 5 ml). The organic phase was applied to a silica gel flash column and eluted with DCM/ethanol/ammonia (250:8:1), which after evaporation of the solvents under vacuum gave N-{4'-[(cyclopropylamino)carbonyl]-6-methyl-1, 1'-biphenyl-3-yl}-2-pyrrolidin-1-ylisonicotinamide (12 mg, 27%). NMR; δH [$^2$H$_6$]—DMSO 10.27,(1H, s), 8.49,(1H, d), 8.19,(1H, d), 7.89,(2H, d), 7.70,(1H, dd), 7.64,(1H, d), 7.43,(2H, d), 7.29,(1H, d), 6.96,(1H, d), 6.85,(1H, s), 3.43,(4H, m), 2.86,(1H, m), 2.19,(3H, s), 1.95,(4H, m), 0.70,(2H, m), 0.59,(2H, m). LCMS: retention time 2.64 min, M$^+$441.

b) 2'-Methyl-5'-[(2-pyrrolidin-1-ylisonicotinoyl)amino]-1,1'-biphenyl-4-carboxylic acid 5'-[(2-Chloroisonicotinoyl)amino]-2'-methyl-1,1'-biphenyl-4-carboxylic acid (600 mg, 1.64 mmol) and pyrrolidine (0.6 ml) were heated in a sealed tube at 90° C. for 5 h. The excess pyrrolidine was evaporated under vacuum and the residue purified by flash chromatography (silica) eluting with DCM/ethanol/ammonia (20:8:1). The solvents were evaporated under vacuum to give 2'-methyl-5'-[(2-pyrrolidin-1-ylisonicotinoyl)amino]-1,1'-biphenyl-4-carboxylic acid (546 mg, 83%). LCMS: retention time 2.74 min, MH$^+$402.

c) 5'-[(2-Chloroisonicotinoyl)amino]-2'-methyl-1,1'-biphenyl-4-carboxylic acid Methyl 5'-[(2-chloroisonicotinoyl)amino]-2'-methyl-1,1'-biphenyl-4-carboxylate (1.63 g, 4.28 mmol) and lithium hydroxide monohydrate (376 mg, 9.0 mmol) were mixed in water (5 ml) and THF (10 ml) and stirred at room temperature for 90 h. The pH was adjusted to pH3 by addition of hydrochloric acid (2N) and the mixture extracted with ethyl acetate (3×50 ml). The combined extracts were washed with water (75 ml), brine (75 ml), dried (magnesium sulphate) and concentrated under vacuum. The residue was purified by flash column chromatography on silica eluting with DCM/ethanol/ammonia (30:8:1 then 20:8:1). The solvents were evaporated under vacuum to give 5'-[(2-chloroisonicotinoyl)amino]-2'-methyl-1,1'-biphenyl-4-carboxylic acid (1.15 g, 73%). LCMS: retention time 3.53 min, MH$^+$367.

d) Methyl 5'-[(2-chloroisonicotinoyl)amino]-2'-methyl-1, 1'-biphenyl-4-carboxylate 2-Chloropyridine-4-carbonyl chloride (1.58 g, 9.0 mmol) in DCM (10 ml) was added dropwise to a solution of methyl 5'-amino-2'-methyl-1,1'-biphenyl-4-carboxylate (1.81 g, 7.5 mmol) and triethylamine (3.13 ml, 22.5 mmol) in DCM (10 ml) at 0° C. The reaction was stirred at room temperature for 20 h, the solvent evaporated under vacuum and the residue partitioned between ethyl acetate (50 ml) and saturated aqueous sodium bicarbonate (50 ml). The aqueous was extracted with ethyl acetate (50 ml) and the combined organic phases washed with brine (50 ml), dried (magnesium sulphate) and the solvent evaporated under vacuum. The residue was purified by flash column chromatography on silica eluting with DCM/ethanol/ammonia (300:8:1). The solvents were evaporated under vacuum to give methyl 5'-[(2-chloroisonicotinoyl) amino]-2'-methyl-1,1'-biphenyl-4- carboxylate (1.73 g, 61%). LCMS: retention time 3.69 min, MH$^+$381.

e) Methyl 5'-amino-2'-methyl-1,1-biphenyl-4-carboxylate 3-Bromo-4-methylaniline (744 mg, 4.0 mmol), (4-methoxycarbonylphenyl)boronic acid (864 mg, 4.8 mmol), tetrakis(triphenylphosphine)palladium (100 mg, 0.087 mmol) and caesium carbonate (2.4 g, 7.37 mmol) were mixed in DME (30 ml) and heated at 90° C. for 20 h. The reaction was absorbed onto silica applied to a silica SPE (10 g) and eluted with ethyl acetate/cyclohexane (0-100% ethyl acetate). The solvent was evaporated from the product fractions under vacuum to give methyl 5'-amino-2'-methyl-1,1'-biphenyl-4- carboxylate (500 mg, 43%). NMR; δH CDCl$_3$ 8.07,(2H, d), 7.38,(2H, d), 7.07,(1H, d), 6.67,(1H, dd), 6.60,(1H, d), 3.94,(3H, s), 2.14,(3H, s).

Example 28

N-(4'-{[(Cyclopropylmethyl)amino]carbonyl}-6-methyl-1,1'-biphenyl-3-yl)-5-(pyrid-2-yl)thiophene-2-carboxamide N-(4'-{[(Cyclopropylmethyl)amino]carbonyl}-6-methyl-1,1'-biphenyl-3-yl)-5-(pyrid-2-yl)thiophene-2- carboxamide was prepared from 5'-amino-N-(cyclopropylmethyl)-2'-methyl-1,1'-biphenyl-4-carboxamide and 5-(pyrid-2-yl) thiophene-2-carboxylic acid using method D. The product was further purified by preparative HPLC. NMR; δH [$^2$H$_6$]—DMSO 10.29,(1H, s), 8.63,(1H, t), 8.58,(1H, d), 8.02-7.99, (2H, m), 7.94,(2H, d), 7.90-7.86,(2H, m), 7.70,(1H, dd), 7.65, (1H, d), 7.46,(2H, d), 7.35,(1H, m), 7.30,(1H, d), 3.17,(2H, t), 2.21,(3H, s), 1.04,(1H, m), 0.43,(2H, m), 0.24,(2H, m). LCMS: retention time 3.60 min, MH$^+$468.

Example 29

5-(4-Chlorophenyl)-N-(4'-{[(cyclopropylmethyl) amino]carbonyl}-6-menthyl-1,1'-biphenyl-3-yl)-2-furamide 5'-Amino-N-(cyclopropylmethyl)-2'-methyl-1,1'-biphenyl-4-carboxamide (53 mg, 0.189 mmol) and 5-(4-chlorophenyl)-2-furoic acid (84.2 mg, 0.378 mmol) were mixed in THF (5 ml) and the mixture shaken in a varian tube for 15 min at room temperature. Carbodiimde resin (500 mg) was added and shaking continued for 18 h. The solution was filtered off and concentrated under vacuum. The residue was dissolved in methanol, filtered through an SCX SPE and the solvent evaporated under vacuum to give 5-(4-chlorophenyl)-N-(4'-{[(cyclopropylmethyl)amino]carbonyl}-6-methyl-1,1'-biphenyl-3-yl)-2- furamide (10 mg, 11%). NMR; δH CDCl$_3$ 8.07,(1H, b), 7.85,(2H, d), 7.69-7.65,(3H, m), 7.52, (1H, d), 7.44-7.41,(4H, m), 7.31-7.29,(2H, m), 6.98,(1H, b), 6.79,(1H, d), 3.36,(2H, m), 2.25,(3H, s), 1.10,(1H, m), 0.60, (2H, m), 0.31,(2H, m). LCMS: retention time 3.92 min, MH$^+$485.

Example 30

N-(4'-{[(Cyclopropylmethyl)amino]carbonyl}-6-methyl-1,1'-biphenyl-3-yl)-2-methyl-5-phenyl-3-furamide 5'-Amino-N-(cyclopropylmethyl)-2'-methyl-1,1'-biphenyl-4-carboxamide (53 mg, 0.189 mmol) and 2-methyl-5-phenyl-3-furoic acid (76.4 mg, 0.378 mmol) were mixed in THF (5 ml) and the mixture shaken in a varian tube for 15 min at room temperature. Carbodiimde resin (500 mg) was added and shaking continued for 18 h. The solution was filtered off and concentrated under vacuum. The residue was dissolved in methanol, filtered through an SCX SPE and the solvent evaporated under vacuum to give N-(4'-{[(cyclopropylmethyl)amino]carbonyl}-6-methyl-1,1'-biphenyl-3-yl)-2-methyl-5-phenyl-3-furamide (24 mg, 28%). NMR; δH CDCl$_3$ 7.81,(2H, d), 7.64,(2H, d), 7.55-7.53,(2H, m), 7.45,(1H, s), 7.40-7.37,(4H,m), 7.30-7.25,(2H,m), 6.78,(1H, s), 6.26,(1H, t), 3.33,(2H, t), 2.70,(3H, s), 2.22,(3H, s), 1.07,(1H, m), 0.57, (2H, m), 0.28,(2H, m). LCMS: retention time 3.93 min, MH$^+$465.

Example 31

N-(4'-{[(Cyclopropylmethyl)amino]carbonyl}-6-methyl-1,1'-biphenyl-3-yl)-2-(Pyrid-3-yl)thiazole-4-carboxamide N-(4'-{[(Cyclopropylmethyl)amino]carbonyl}-6-methyl-1,1'-biphenyl-3-yl)-2-(pyrid-3-yl)thiazole-4-carboxamide was prepared from 5'-amino-N-(cyclopropylmethyl)-2'-methyl-1,1'-biphenyl-4-carboxamide and 2-(pyrid-3-yl)thiazole-4-carboxylic acid using method D. NMR; δH CDCl$_3$ 9.26,(1H, b), 9.24,(1H, d), 8.73,(1H, d), 8.28,(2H, m), 7.85, (2H, d), 7.72,(1H, dd), 7.60,(1H, d), 7.47-7.44,(3H, m), 7.32, (1H, d), 6.29,(1H, t), 3.36,(2H, m), 2.26,(3H, s), 1.10,(1H, m), 0.59,(2H, m), 0.31,(2H, m). LCMS: retention time 3.36 min, MH$^+$469.

Example 32

N-(4'-{[(Cyclopropylmethyl)amino]carbonyl}-6-methyl-1,1'-biphenyl-3-yl)-4-methyl-2-(pyrid-3-yl)thiazole-5-carboxamide N-(4'-{[(Cyclopropylmethyl)amino]carbonyl}-6-methyl-1,1'-biphenyl-3-yl)-4-methyl-2-(pyrid-3-yl)thiazole-5- carboxamide was prepared from 5'-amino-N-(cyclopropylmethyl)-2'-methyl-1,1'-biphenyl-4-carboxamide and 4-methyl-2-(pyrid-3-yl)thiazole-5-carboxylic acid using method D. NMR; δH CDCl$_3$ 9.18,(1H, b), 8.72,(1H, b), 8.27, (1H, d), 7.84,(2H, d), 7.59,(1H, s), 7.55,(1H, dd), 7.45-7.40, (4H, m), 7.30,(1H, d), 6.27,(1H, t), 3.36,(2H, m), 2.83,(3H, s), 2.25,(3H, s), 1.09,(1H, m), 0.58,(2H, m), 0.30,(2H, m). LCMS: retention time 3.41 min, MH$^+$483.

Example 33

N-(4'-{[(Cyclopropylmethyl)amino]carbonyl}-6-methyl-1,1'-biphenyl-3-yl)-1-ethyl-3-(thiophen-2-yl)pyrazole-5-carboxamide N-(4'-{[(Cyclopropylmethyl)amino]carbonyl}-6-methyl-1,1'-biphenyl-3-yl)-1-ethyl-3-(thiophen-2-yl)pyrazole-5-carboxamide was prepared from 5'-amino-N-(cyclopropylmethyl)-2'-methyl-1,1'-biphenyl-4-carboxamide and 1-ethyl-3-(thiophen-2-yl)pyrazole-5- carboxylic acid using method D. NMR; δH CDCl$_3$ 8.02,(1H, b), 7.86-7.83,(3H, m), 7.57, (1H, dd), 7.47,(1H, d), 7.40,(2H, d), 7.34,(1H, m), 7.30-7.26, (3H, m), 7.07,(1H, m), 4.63,(2H, q), 3.35,(2H, m), 2.24,(3H, s), 1.08,(1H, m), 0.58,(2H, m), 0.30,(2H, m). LCMS: retention time 3.81 min, MH$^+$485.

Example 34

N-(4'-{[(Cyclopropylmethyl)amino]carbonyl}-6-methyl-1,1'-biphenyl-3-yl)-2-(fur-2-yl)acetamide N-(4'-{[(Cyclopropylmethyl)amino]carbonyl}6-methyl-1,1'-biphenyl-3-yl)-2-(fur-2-yl)acetamide was prepared from 5'-amino-N-(cyclopropylmethyl)-2'-methyl-1,1'-biphenyl-4- carboxamide and fur-2-ylacetic acid using method D. NMR; δH [$^2$H$_6$]—DMSO 10.17,(1H, s), 8.61,(1H, t), 7.91, (2H, d), 7.55,(1H, m), 7.50-7.48,(2H, m), 7.40,(2H, d), 7.23, (1H, d), 6.38,(1H, m), 6.25,(1H, d), 3.70,(2H, s), 3.16,(2H, t), 2.16,(3H, s), 1.04,(2H, m), 0.42,(2H, m). LCMS: retention time 3.26 min, MH$^+$389.

Example 35

N-(4'-{[(Cyclopropylmethyl)amino]carbonyl}-6-methyl-1,1'-biphenyl-3-yl)cyclobutanecarboxamide N-(4'-{[(Cyclopropylmethyl)amino]carbonyl}-6-methyl-1,1'-biphenyl-3-yl)cyclobutanecarboxamide was prepared from 5'-amino-N-(cyclopropylmethyl)-2'-methyl-1,1'-biphenyl-4-carboxamide and cyclobutanecarboxylic acid using method D. NMR; δH [$^2$H$_6$]—DMSO 9.71,(1H, s), 8.61,(1H, t), 7.91,(2H, d), 7.52-7.49,(2H, m), 7.40,(2H, d), 7.21,(1H, d), 3.21-3.14,(3H, m), 2.24-2.15,(5H, m), 2.07,(2H, m), 1.91, (1H, m), 1.78,(1H, m), 1.04,(1H, m), 0.43,(2H, m), 0.24,(2H, m). LCMS: retention time 3.30 min, MH$^+$363.

Example 36

N-(4'-{[(Cyclopropylmethyl)amino]carbonyl}-6-methyl-1,1'-biphenyl-3-yl)cyclopropanecarboxamide N-(4'-{[(Cyclopropylmethyl)amino]carbonyl}-6-methyl-1,1'-biphenyl-3-yl)cyclopropanecarboxamide was prepared from 5'-amino-N-(cyclopropylmethyl)-2'-methyl-1,1'-biphenyl-4-carboxamide and cyclopropanecarboxylic acid using method D. NMR; δH [$^2$H$_6$]—DMSO 10.18,(1H, s), 8.60,(1H, t), 7.91,(2H, d), 7.50-7.47,(2H, m), 7.40,(2H, d), 7.21,(1H, d), 3.16,(2H, t), 2.16,(3H, s), 1.74,(1H, m),1.04,(1H, m), 0.77-0.75,(4H, m), 0.43,(2H, m), 0.23,(2H, m). LCMS: retention time 3.19 min, MH$^+$349.

Example 37

N-(4'-{[(Cyclopropylmethyl)amino]carbonyl}-6-methyl-1,1'-biphenyl-3-yl)-2-furamide N-(4'-{[(Cyclopropylmethyl)amino]carbonyl}-6-methyl-1,1'-biphenyl-3-yl)-2-furamide was prepared from 5'-amino-N-(cyclopropylmethyl)-2'-methyl-1,1'-biphenyl-4-carboxamide and 2-furoic acid using method D. NMR; δH [$^2$H$_6$]—DMSO 10.18,(1H, s), 8.62,(1H, t), 7.93-7.91,(3H, m), 7.69,(1H, dd), 7.65,(1H, d), 7.44,(2H, d), 7.31,(1H, d), 7.27,(1H, d), 6.69,(1H, m), 3.16,(2H, m), 2.19,(3H, s), 1.04,(1H, m), 0.43,(2H, m), 0.24,(2H, m). LCMS: retention time 3.25 min, MH$^+$375.

Example 38

N-(4'-{[(Cyclopropylmethyl)amino]carbonyl}-6-methyl-1,1'-biphenyl-3-yl)thiophene-3-carboxamide N-(4'-{[(Cyclopropylmethyl)amino]carbonyl}-6-methyl-1,1'-biphenyl-3-yl)thiophene-3-carboxamide was prepared from 5'-amino-N-(cyclopropylmethyl)-2'-methyl-1,1'-biphenyl-4-carboxamide and 3-thiophene carboxylic acid using method D. NMR; δH [$^2$H$_6$]—DMSO 10.05,(1H, s), 8.62,(1H, t), 8.32,(1H, m), 7.93,(2H, d), 7.69,(1H, dd), 7.65-7.61,(3H, m), 7.44,(2H, d), 7.28,(1H, d), 3.16,(2H, t), 2.20,(3H, s), 1.04,(1H, m), 0.44,(2H, m), 0.24,(2H, m). LCMS: retention time 3.41 min, MH$^+$391.

Example 39

N-(4'-{[(Cyclopropylmethyl)amino]carbonyl}-6-methyl-1,1'-biphenyl-3-yl)cyclopentanecarboxamide N-(4'{[(Cyclopropylmethyl)amino]carbonyl}-6-methyl-1,1'-biphenyl-3-yl)cyclopentanecarboxamide was prepared from 5'-amino-N-(cyclopropylmethyl)-2'-methyl-1,1'-biphenyl-4-carboxamide and cyclopentanecarboxylic acid using method D. NMR; δH [$^2$H$_6$]—DMSO 9.85,(1H, s), 8.61,(1H, t), 7.91,(2H, d), 7.52-7.49,(2H, m), 7.40,(2H, d), 7.20,(1H, d), 3.16,(2H, t), 2.74,(1H, m), 2.15,(3H, s), 1.83-1.51,(8H, m), 1.04,(1H, m), 0.43,(2H, m), 0.24,(2H, m). LCMS: retention time 3.42 min, MH$^+$377.

Example 40

N-(4'-{[(Cyclopropylmethyl)amino]carbonyl}-6-methyl-1,1'-biphenyl-3-yl)tetrahydropyran-4-carboxamide N-(4'-{[(Cyclopropylmethyl)amino]carbonyl}-6-methyl-1,1'-biphenyl-3-yl)tetrahydropyran-4- carboxamide was prepared from 5'-amino-N-(cyclopropylmethyl)-2'-methyl-1,1'-biphenyl-4- carboxamide and tetrahydropyran-4-carboxylic acid using method D. NMR; δH [$^2$H$_6$]—DMSO 9.89,(1H, s), 8.61,(1H, t), 7.91,(2H, d), 7.52-7.48,(2H, m), 7.40,(2H, d), 7.21,(1H, d), 3.89,(2H, m), 3.37,(1H, m), 3.16,(2H, t), 2.56,(2H, m), 2.16,(3H, s), 1.65,(3H, m), 1.04,(1H, m), 0.43,(2H, m), 0.24,(2H, m). LCMS: retention time 2.94 min, MH$^+$393.

Example 41

N-(4'-{[(Cyclopropylmethyl)amino]carbonyl}-6-methyl-1,1'-biphenyl-3-yl)tetrahydrofuran-2-carboxamide N-(4'-{[(Cyclopropylmethyl)amino]carbonyl}-6-methyl-1,1'biphenyl-3-yl)tetrahydrofuran-2- carboxamide was prepared from 5'-amino-N-(cyclopropylmethyl)-2'-methyl-1,1'-biphenyl-4- carboxamide and tetrahydrofuran-2-carboxylic acid. using method D. NMR; δH [$^2$H$_6$]—DMSO 9.65,(1H, s), 8.61,(1H, t), 7.91,(2H, d), 7.63-7.60,(2H, m), 7.41,(2H, d), 7.22,(1H, d), 4.36,(1H, m), 3.97,(1H, q), 3.81,(1H, q), 3.16,(2H, t), 2.17,(4H, m), 1.97,(1H, m), 1.84,(2H, m), 1.04,(1H, m), 0.43,(2H, m), 0.24,(2H, m). LCMS: retention time 3.12 min, MH$^+$379.

Example 42

N-(4'-{[(Cyclopropylmethyl)amino]carbonyl}-6-methyl-1,1'-biphenyl-3-yl)thiazole-4-carboxamide N-(4'-{[(Cyclopropylmethyl)amino]carbonyl}-6-methyl-1,1'-biphenyl-3-yl)thiazole-4-carboxamide was prepared from 5'-amino-N-(cyclopropylmethyl)-2'-methyl-1,1'-biphenyl-4- carboxamide and thiazole-4-carboxylic acid using method D. NMR; δH [$^2$H$_6$]—DMSO 10.35, (1H, s), 9.26, (1H, d), 8.62,(1H, t), 8.47,(1H, d), 7.92,(2H, d), 7.78-7.76, (2H, m), 7.44,(2H, d), 7.28,(1H, d), 3.16,(2H, t), 2.20,(3H, s), 1.04,(1H, m), 0.44,(2H, m), 0.24,(2H, m). LCMS: retention time 3.25 min, MH$^+$392.

Example 43

N-(4'-{[(Cyclopropylmethyl)amino]carbonyl}-6-methyl-1,1'-biphenyl-3-yl)isoxazole-5-carboxamide N-(4'-{[(Cyclopropylmethyl)amino]carbonyl}-6-methyl-1,1'-biphenyl-3-yl)isoxazole-5-carboxamide was prepared from 5'-amino-N-(cyclopropylmethyl)-2'-methyl-1,1'-biphenyl-4- carboxamide and isoxazole-5-carboxylic acid using method D. NMR; δH [$^2$H$_6$] —DMSO 10.75, (1H, s), 8.81, (1H, d), 8.62,(1H, t), 7.93,(2H, d), 7.70,(1H, dd), 7.66,(1H, d), 7.44,(2H, d), 7.32,(1H, d), 7.24,(1H, d), 3.16,(2H, t), 2.21,(3H, s), 1.04,(1H, m), 0.43,(2H, m), 0.24,(2H, m). LCMS: retention time 3.17 min, MH$^+$376.

Example 44

5-Bromo-N-(4'-{[(cyclopropylmethyl)amino]carbonyl}-6-methyl-1,1'-biphenyl-3-yl)nicotinamide 5'-Amino-N-(cyclopropylmethyl)-2'-methyl-1,1'-biphenyl-4-carboxamide (26.4 mg, 0.009 mmol) and 5-bromonicotinic acid (38 mg, 0.18 mmol) were mixed in THF (2 ml) and the mixture shaken in a varian tube for 5 min at room temperature. Carbodiimde resin (250 mg, 0.27 mmol) was added and shaking continued for 72 h. The solution was filtered off and concentrated under vacuum. The residue was chromatographed on a silica gel flash column eluting with ethyl acetate/hexane (1:2 then 1:1) and the solvent evaporated under vacuum to give 5-bromo-N-(4'-{[(cyclopropylmethyl)amino]carbonyl}-6-methyl1,1'-biphenyl-3-yl)nicotinamide (37 mg, 85%). NMR; δH [2H$_6$]—DMSO 10.50,(1H, s), 9.05, (1H, m), 8.90,(1H, m), 8.62,(1H, t), 8.54,(1H, t), 7.93,(2H, d), 7.70,(1H, dd), 7.66,(1H, d), 7.44,(2H, d), 7.31,(1H, d), 3.16, (2H, t), 2.21,(3H, s), 1.04,(1H, m), 0.43,(2H, m). LCMS: retention time 3.44 min, MH$^+$464/466.

Example 45

N-(4'{[(Cyclopropylmethyl)amino]carbonyl}-6-methyl-1,1'-biphenyl-3-yl)-2-phenylpyrimidine-4-carboxamide 5'-Amino-N-(cyclopropylmethyl)-2'-methyl-1,1'-biphenyl-4-carboxamide (53 mg, 0.189 mmol) and 2-phenylpyrimidine-4-carboxylic acid (99.5 mg, 0.50 mmol) were mixed in THF (5 ml) and the mixture shaken in a varian tube for 15 min at room temperature. Carbodiimde resin (500 mg) was added and shaking continued for 48 h. The solution was filtered off and concentrated under vacuum. The residue was chromatographed on a silica gel flash column eluting with ethyl acetate/hexane (1:1) and the solvent evaporated under vacuum to give N-(4'-{[(cyclopropylmethyl)amino]carbonyl}-6methyl-1,1'-biphenyl-3-yl)-2-phenylpyrimidine-4-carboxamide (13 mg). NMR; $\delta$H CDCl$_3$ 9.98,(1H, s), 9.09, (1H, d), 8.50-8.47,(2H, m), 8.08,(1H, d), 7.86,(2H, d), 7.70, (1H, dd), 7.63,(1H, d), 7.56-7.54,(3H, m), 7.45,(2H, d), 7.33, (1H, d), 7.26,(1H, m), 3.36,(2H, m), 2.26,(3H, s), 1.09,(1H, m), 0.58,(2H, m), 0.30,(2H, m). LCMS: retention time 3.88 min, MH$^+$463.

Example 46

5-Chloro-N-(4'-{[(cyclopropylmethyl)amino]carbonyl}-6-methyl-1,1'-biphenyl-3-yl)-2-(piperidin-1-yl)pyrimidine-4-carboxamide 5'-Amino-N-(cyclopropylmethyl)-2'-methyl-1,1'-biphenyl-4-carboxamide (53 mg, 0.189 mmol) and 5-chloro-2-(piperidin-1-yl)pyrimidine-4-carboxylic acid (91.3 mg, 0.38 mmol) were mixed in THF (5 ml) and the mixture shaken in a varian tube for 15 min at room temperature. Carbodiimde resin (500 mg) was added and shaking continued for 48 h. The solution was filtered off and concentrated under vacuum. The residue was chromatographed on a silica gel flash column eluting with ethyl acetate/hexane (1:1) and the solvent evaporated under vacuum to give 5-chloro-N-(4'-{[(cyclopropylmethyl)amino]carbonyl}-6-methyl-1,1'-biphenyl-3-yl)-2-(piperidin-1-yl)pyrimidine-4- carboxamide (35 mg). NMR; $\delta$H CDCl$_3$ 9.50,(1 H, s), 8.40,(1 H, s), 7.83,(2H, d), 7.64,(1H, dd), 7.56,(1H, d), 7.41,(2H, d), 7.27,(1H, d), 6.24,(1H, t), 3.79,(4H, m), 3.35,(2H, m), 2.22,(3H, s), 1.65,(4H, m), 1.08, (1H, m), 0.82,(2H, m), 0.58,(2H, m), 0.30,(2H, m). LCMS: retention time 3.96 min, MH$^+$504.

Example 47

5-Chloro-N-(4'-{[(cyclopropylmethyl)amino]carbonyl}-6-methyl-1,1'-biphenyl-3-yl)-2-hexamethyleneiminopyrimidine-4-carboxamide 5'-Amino-N-(cyclopropylmethyl)-2'-methyl-1,1'-biphenyl carboxamide (53 mg, 0.189 mmol) and 5chloro-2-hexamethyleneiminopyrimidine-4-carboxylic acid (52.2 mg, 0.20 mmol) were mixed in THF (5 ml) and the mixture shaken in a varian tube for 15 min at room temperature. Carbodiimde resin (500 mg) was added and shaking continued for 48 h. The solution was filtered off and concentrated under vacuum. The residue was chromatographed on a silica gel flash column eluting with ethyl acetate/hexane (1:1) and the solvent evaporated under vacuum to give 5-chloro-N-(4'-{[(cyclopropylmethyl)amino]carbonyl}-6-methyl-1,1'-biphenyl-3-yl)-2-hexamethyleneiminopyrimidine-4- carboxamide (14 mg). NMR; $\delta$H CDCl$_3$ 9.65,(1H, s), 8.41,(1H, s), 7.83,(2H, d), 7.61,(1H, dd), 7.56,(1H, d), 7.41,(2H, d), 7.27,(1H, d), 6.24,(1H, m), 3.76, (4H, m), 3.35,(2H, m), 2.23,(3H, s), 1.81,(4H, m), 1.09, (1H, m), 0.82,(4H, m), 0.58,(2H, m), 0.30,(2H, m). LCMS: retention time 4.06 min, MH$^+$518.

Example 48

N-(4'-{[(Cyclopropylmethyl)amino]carbonyl}-6-methyl-1,1'-biphenyl-3-yl)-3-(2,5-dimethylpyrrol-1-yl)benzamide 5'-Amino-N-(cyclopropylmethyl)-2'-methyl-1,1'-biphenyl-4-carboxamide (53 mg, 0.189 mmol) and 3-(2,5-dimethylpyrrol-1-yl)benzoic acid (122 mg, 0.57 mmol) were mixed in THF (5 ml) and the mixture shaken in a varian tube for 15 min at room temperature. Carbodiimde resin (500 mg) was added and shaking continued for 18 h. The solution was filtered off and concentrated under vacuum. The residue chromatographed on a silica gel flash column eluting with ethyl acetate/hexane (1:1) and the solvent evaporated under vacuum to give N-(4'-{[(cyclopropylmethyl)amino]carbonyl}-6-methyl-1,1'-biphenyl-3-yl)-3-(2,5-dimethylpyrrol1-yl)benzamide (75 mg, 74%). NMR; $\delta$H CDCl$_3$ 7.91,(1H, d), 7.83,(2H, d), 7.79,(1H, s), 7.71,(1H, s), 7.61-7.55,(2H, m), 7.49,(1H, s), 7.41,(3H, m), 7.29,(1H, d), 6.24,(1H, m), 5.92, (2H, s), 3.34,(2H, m), 2.23,(3H, s), 2.04,(6H, s), 1.08,(1H, m), 0.57,(2H, m), 0.29,(2H, m). LCMS: retention time 3.80 min, MH$^+$478.

Example 49

N-(4'-{[(Cyclopropylmethyl)amino]carbonyl}-6-methyl-1,1'-biphenyl-3-yl)-3-(4-trifluoromethylphenyl)benzamide 5'-Amino-N-(cyclopropylmethyl)-2'-methyl-1,1'-biphenyl-4-carboxamide (53 mg, 0.189 mmol) and 3-(4-trifluoromethylphenyl)benzoic acid (151 mg, 0.57 mmol) were mixed in THF (5 ml) and the mixture shaken in a varian tube for 15 min at room temperature. Carbodiimde resin (500 mg) was added and shaking continued for 18 h. The solution was filtered off and concentrated under vacuum. The residue was chromatographed on a silica gel flash column eluting with ethyl acetate/hexane (1:1) and the solvent evaporated under vacuum to give N-(4'-{[(cyclopropylmethyl)amino]carbonyl}-6-methyl-1,1'-biphenyl-3-yl)-3-(4-trifluoromethylphenyl)benzamide (67 mg, 67%). NMR; $\delta$H CDCl$_3$ 8.11,(1H, t), 7.87-7.85,(2H, m), 7.83,(2H, d), 7.77,(1H, m), 7.72,(4H, s), 7.63-7.57,(2H, m), 7.50,(1H, d), 7.41,(2H, d), 7.30,(1H, d), 6.25,(1H, t), 3.34,(2H, m), 2.24,(3H, s), 1.08,(1H, m), 0.57, (2H, m), 0.29,(2H, m). LCMS: retention time 4.01 min, MH$^+$529.

Example 50

N-(4'-{[(Cyclopropylmethyl)amino]carbonyl}-6-methyl-1,1'-biphenyl-3-yl)-4-methoxy-3-phenylbenzamide 5'-Amino-N-(cyclopropylmethyl)-2'-methyl-1,1'-biphenyl-4-carboxamide (53 mg, 0.189 mmol) and 4-methoxy-3-phenylbenzoic acid (129 mg, 0.57mmol) were mixed in THF (5 ml) and the mixture shaken in a varian tube for 15 min at room temperature. Carbodiimde resin (500 mg) was added and shaking continued for 18 h. The solution was filtered off and concentrated under vacuum. The residue was chromatographed on a silica gel flash column eluting with ethyl acetate/ hexane (1:2) and the solvent evaporated under vacuum to give N-(4'-{[(cyclopropylmethyl)amino]carbonyl}-6-methyl-1,1'-biphenyl-3-yl)-4-methoxy-3-phenylbenzamide (45 mg). NMR; δH CDCl₃ 7.90, (1H, dd), 7.82-7.79,(4H, m), 7.58, (1H, dd), 7.53-7.33,(5H, m), 7.27-7.25,(1H, m), 7.05,(1H, d), 6.25,(1H, t), 3.87,(3H, s), 3.34,(2H, m), 2.22,(3H, s), 1.08, (1H, m), 0.57,(2H, m), 0.29,(2H, m). LCMS: retention time 3.78 min, MH⁺491.

Example 51

N-(4'-{[(Cyclopropylmethyl)amino]carbonyl}-6-methyl-1,1'-biphenyl-3-yl)-3-(2-oxo-1-pyrrolidine)benzamide 5'-Amino-N-(cyclopropylmethyl)-2'-methyl-1,1'-biphenyl-4-carboxamide (64.2 mg, 0.23 mmol), 3-(2-oxo-1-pyrrolidine)benzoic acid (47 mg, 0.23 mmol), HATU (87 mg, 0.23 mmol), HOBT (31 mg, 0.23 mmol) and DIPEA (118 µl) were stirred in DMF (2 ml) for 18 h at room temperature. The reaction was partitioned between ethyl acetate (100 ml) and hydrochloric acid (0.5M, 20 ml), the organic phase washed with aqueous sodium hydrogen carbonate (saturated) and dried (magnesium sulphate). The solvent was evaporated under vacuum to give N-(4'-{[(cyclopropylmethyl)amino]carbonyl}6-methyl-1,1'-biphenyl-3-yl)-3-(2-oxo-1-pyrrolidine)benzamide (9.0 mg, 84%). NMR; δH [²H₆]—DMSO 10.27,(1H, s), 8.62,(1H, t), 8.09,(1H, m), 7.94-7.90,(3H, m), 7.73-7.67,(3H, m), 7.51,(1H, t), 7.45,(2H, d), 7.29,(1H, d), 3.89,(2H, t), 3.16,(2H, t), 2.54-2.49,(2H, m), 2.20,(3H, s), 2.08,(2H, m), 1.04,(1H, m), 0.44,(2H, m), 0.24,(2H, m). LCMS: retention time 3.25 min, MH⁺468.

Example 52

N-(4'-{[(Cyclopropylmethyl)amino]carbonyl}-6-methyl-1,1'-biphenyl-3-yl)-3-fur-3-ylbenzamide 5'-Amino-N-(cyclopropylmethyl)-2'-methyl-1,1'-biphenyl-4-carboxamide (48 mg, 0.17 mmol), 3-fur-3-ylbenzoic acid (32 mg, 0.17 mmol), HATU (65 mg, 0.17 mmol), HOBT (23 mg, 0.17 mmol) and DIPEA (88 µl) were stirred in DMF (1.5 ml) for 18 h at room temperature. The reaction was partitioned between ethyl acetate (100 ml) and hydrochloric acid (0.5M, 20 ml), the organic phase washed with aqueous sodium hydrogen carbonate (saturated) and dried (magnesium sulphate). The solvent was evaporated under vacuum to give N-(4'-{[(cyclopropylmethyl)amino]carbonyl}-6-methyl-1,1'-biphenyl-3-yl)-3-fur-3-ylbenzamide (61 mg, 79%). NMR; δH [²H₆]—DMSO 10.16,(1H, s), 8.35,(1H, t), 8.22, (1H, s), 7-89,(2H, d), 7.79,(2H, t), 7.69-7.65,(2H, m), 7.56, (1H, s), 7.45,(1H, t), 7.35,(2H, d), 7.19,(1H, d), 6.85,(1H, d), 6.49,(1H, m), 3.17,(2H, t), 2.18,(3H, s), 1.04,(1H, m), 0.42, (2H, m), 0.22,(2H, m). LCMS: retention time 3.75 min, MH⁺451.

Example 53

2-Cyclohexyl-N-(4'-{[cyclopropylmethyl)amino]carbonyl}-6-methyl-1,1'-biphenyl-3-yl)-6methylquinoline-4-carboxamide 5'-Amino-N-(cyclopropylmethyl)-2'-methyl-1,1'-biphenyl-4-carboxamide (42 mg, 0.15 mmol) and 2-cyclohexyl-6-methylquinoline-4-carboxylic acid (107.7 mg, 0.4 mmol) were mixed in THF (5 ml) and the mixture shaken in a varian tube for 30 min at room temperature. Carbodiimde resin (442 mg, 0.5 mmol) was added and shaking continued for 18 h. The solution was filtered off, the resin washed with THF and methanol and the combined filtrate and washings reduced to dryness under vacuum. The residue was dissolved in ethyl acetate, washed with hydrochloric acid (1M) and aqueous sodium hydrogen carbonate. The solvent was evaporated from the organic fraction under vacuum to give 2-cyclohexyl-N-(4'-{[(cyclopropylmethyl)amino]carbonyl}-6-methyl-1,1'-biphenyl-3-yl)-6-methylquinoline-4-carboxamide. NMR; δH [²H₆]—DMSO 10.69,(1H, s), 8.62,(1H, t), 7.95-7.90,(3H, m), 7.82,(1H, s), 7.70,(2H, m), 7.60,(1H, dd, 7.56, (1H, s), 7.46,(2H, d), 7.33,(1H, d), 3.16,(2H, t), 2.90,(1H, m), 2.47, (3H, s), 2.22,(3H, s), 1.95,(2H, m), 1.84,(2H, m), 1.74-1.61, (3H, m), .46-1.26,(3H, m), 1.04,(1H, m), 0.43,(2H, m), 0.24, (2H, m). LCMS: retention time 3.93 min, MH⁺532.

Example 54

2-Cyclopropyl-N-(4'-{[(cyclopropylmethyl)amino]carbonyl}-6-methyl-1,1'-biphenyl-3-yl)quinoline-4-carboxamide 5'-Amino-N-(cyclopropylmethyl)-2'-methyl-1,1'-biphenyl-4-carboxamide (42 mg, 0.15 mmol) and 2-cyclopropylquinoline-4-carboxylic acid (85.3 mg, 0.4 mmol) were mixed in THF (5 ml) and the mixture shaken in a varian tube for 30 min at room temperature. Carbodiimde resin (442 mg, 0.5 mmol) was added and shaking continued for 18 h. The solution was filtered off, the resin washed with THF and methanol and the combined filtrate and washings reduced to dryness under vacuum. The residue was dissolved in ethyl acetate, washed with hydrochloric acid (1M) and aqueous sodium hydrogen carbonate. The solvent was evaporated from the organic fraction under vacuum to give 2-cyclopropyl-N-(4'-{[(cyclopropylmethyl)amino]carbonyl}-6-methyl-1,1'-biphenyl-3-yl)quinoline-4-carboxamide. NMR; δH [²H₆]—DMSO 10.74,(1H, s), 8.62,(1H, t), 8.04,(1H, d), 7.94-7.90,(3H, m), 7.74-7.70,(3H, m), 7.62,(1H, s), 7.53,(1H, m), 7.45,(2H, d), 7.33,(1H, d), 3.16,(2H, t), 2.37,(1H, m), 2.22,(3H, s), 1.15-1.10,(5H, m), 0.43,(2H, m), 0.24,(2H, m). LCMS: retention time 3.61 min, MH⁺476.

Example 55

N-(4'-{[(Cyclopropylmethyl)amino]carbonyl}-6-methyl-1,1'-biphenyl-3-yl)-2-fur-2-ylquinoline-4-carboxamide 5'-Amino-N-(cyclopropylmethyl)-2'-methyl-1,1'-biphenyl-4-carboxamide (42 mg, 0.15 mmol) and 2-fur-2-ylquinoline-4-carboxylic acid (95.7 mg, 0.4 mmol) were mixed in THF (5 ml) and the mixture shaken in a varian tube for 30 min at room temperature. Carbodiimde resin (442 mg, 0.5 mmol) was added and shaking continued for 18 h. The solution was filtered off, the resin washed with THF and methanol and the combined filtrate and washings reduced to dryness under vacuum. The residue was dissolved in ethyl acetate, washed with hydrochloric acid (1M) and aqueous sodium hydrogen carbonate. The solvent was evaporated from the organic fraction under vacuum to give N-(4'-{[(cyclopropylmethyl)amino]carbonyl}-6-methyl-1,1'-biphenyl-3-yl)-2-fur-2-ylquinoline-4-carboxamide. NMR; δH [²H₆]—DMSO 10.85,(1H, s), 8.62,(1H, t), 8.12-8.07,(3H, m), 7.97,(1H, m), 7.94,(2H, d), 7.82,(1H, m), 7.72,(2H, m), 7.63,(1H, m), 7.49-7.45,(3H, m), 7.34,(1H, d), 6.75,(1H, m), 3.16,(2H, t), 2.23, (3H, s), 1.04,(1H, m), 0.43,(2H, m), 0.24,(2H, m). LCMS: retention time 3.69 min, MH⁺502.

Example 56

N-(4'-{[(Cycloproplmethyl)amino]carbonyl}-6-methyl-1,1'-biphenyl-3-yl)-2-methyl-3-furamide 5'-Amino-N-(cyclopropylmethyl)-2'-methyl-1,1'-biphenyl-4-carboxamide (29 mg, 0.10 mmol) and 2-methyl-3-furoic acid (26.1 mg, 0.21 mmol) were mixed in THF (2.5 ml) and the mixture shaken in a varian tube for 30 min at room temperature. Carbodiimde resin (270 mg, 0.31 mmol) was added and shaking continued for 18 h. A further portion of 2-methyl-3-furoic acid (13.0 mg, 0.10 mmol) was added and shaking continued for 72 h. The solution was filtered off, the resin washed with THF and methanol and the combined filtrate and washings reduced to dryness under vacuum. The residue was dissolved in methanol and filtered through an SPE (SCX), to give, after evaporation of the solvent under vacuum, N-(4'-{[(cyclopropylmethyl)amino]carbonyl}-6-methyl-1,1'-biphenyl-3-yl)-2-methyl-3-furamide. NMR; δH [$^2$H$_6$]—DMSO 9.69,(1H, s), 8.62,(1H, t), 7.92,(2H, d), 7.65, (1H, dd), 7.62,(1H, d), 7.58,(1H, d), 7.44,(2H, d), 7.26,(1H, d), 7.06,(1H, d), 3.16,(2H, t), 2.53,(3H, s), 2.19,(3H, s), 1.04, (1H, m), 0.43,(2H, m), 0.24,(2H, m). LCMS: retention time 3.33 min, MH$^+$389.

Example 57

N-(4'-{[Cyclopropylmethyl)amino]carbonyl}-6-methyl-1,1'-biphenyl-3-yl)cyclopropylacetamide 5'-Amino-N-(cyclopropylmethyl)-2'-methyl-1,1'-biphenyl-4-carboxamide (30 mg, 0.11 mmol) and cyclopropylacetic acid (25 mg, 0.25 mmol) were mixed in THF (3 ml). Carbodiimde resin (295 mg, 0.31 mmol) was added and shaking continued for 72 h. The reaction was filtered, the resin washed with THF and methanol and the combined filtrate and washings filtered through an SPE (SCX), to give, after evaporation of the solvent under vacuum, N-(4'-{[(cyclopropylmethyl)amino]carbonyl}-6-methyl-1,1'-biphenyl-3-yl)cyclopropylacetamide. NMR; δH [$^2$H$_6$]—DMSO 9.81,(1H, s), 8.62,(1H, t), 7.92,(2H, d), 7.52-7.50,(2H, m), 7.42,(2H, d), 7.23,(1H, d), 3.17,(2H, t), 2.20-2.17,(5H, m), 1.09-1.01,(2H, m), 0.49-0.42,(4H, m), 0.25,(2H, m), 0.19,(2H, m). LCMS: retention time 3.15 min, MH$^+$363.

Example 58

N-(4'-{[(Cyclopropylmethyl)amino]carbonyl}-6-methyl-1,1'-biphenyl-3-yl)propionamide 5'-Amino-N-(cyclopropylmethyl)-2'-methyl-1,1'-biphenyl-4-carboxamide (30 mg, 0.11 mmol) and propionic acid (18.5 mg, 0.25 mmol) were mixed in THF (3 ml). Carbodiimde resin (295 mg, 0.31 mmol) was added and shaking continued for 72 h. The reaction was filtered, the resin washed with THF and methanol and the combined filtrate and washings filtered through an SPE (SCX), to give, after evaporation of the solvent under vacuum, N-(4'-{[(cyclopropylmethyl)amino]carbonyl}-6-methyl-1,1'-biphenyl-3-yl)propionamide. NMR; δH [$^2$H$_6$]—DMSO 9.84,(1H, s), 8.60,(1H, t), 7.91,(2H, d), 7.50-7.47,(2H, m), 7.40,(2H, d), 7.21,(1H, d), 3.16,(2H, t), 2.29,(2H, q), 2.15,(3H, s), 1.08-1.02,(4H, m), 0.43,(2H, m), 0.24,(2H, m). LCMS: retention time 3.00 min, MH$^+$337.

Example 59

N-(4'-{[(Cyclopropylmethyl)amino]carbonyl}-6-methyl-1,1'-biphenyl-3-yl)butyramide 5'-Amino-N-(cyclopropylmethyl)-2'-methyl-1,1'-biphenyl-4-carboxamide (30 mg, 0.11 mmol) and butyric acid (22.0 mg, 0.25 mmol) were mixed in THF (3 ml). Carbodiimde resin (295 mg, 0.31 mmol) was added and shaking continued for 72 h. The reaction was filtered, the resin washed with THF and methanol and the combined filtrate and washings filtered through an SPE (SCX), to give, after evaporation of the solvent under vacuum, N-(4'-{[(cyclopropylmethyl)amino]carbonyl}-6-methyl-1,1'-biphenyl-3-yl)butyramide. NMR; δH [$^2$H$_6$]—DMSO 9.85,(1H, s), 8.60,(1H, t), 7.91, (2H, d), 7.50-7.49,(2H, m), 7.40,(2H, d), 7.21,(1H, d), 3.16, (2H, t), 2.25,(2H, t), 2.15,(3H, s), 1.59,(2H, m), 1.04,(1H, m), 0.89,(3H, t), 0.43,(2H, m), 0.24,(2H, m). LCMS: retention time 3.14 min, MH$^+$351.

Example 60

N-(4'-{[(Cyclotpropylmethyl)amino]carbonyl}-6-methyl-1,1'-biphenyl-3-yl)acetamide 5'-Amino-N-(cyclopropylmethyl)-2'-methyl-1,1'-biphenyl-4-carboxamide (30 mg, 0.11 mmol) and acetic acid (15.0 mg, 0.25 mmol) were mixed in THF (3 ml). Carbodiimde resin (295 mg, 0.31 mmol) was added and shaking continued for 72 h. The reaction was filtered, the resin washed with THF and methanol and the combined filtrate and washings filtered through an SPE (SCX), to give, after evaporation of the solvent under vacuum, N-(4'-{[(cyclopropylmethyl)amino]carbonyl}-6-methyl-1,1'-biphenyl-3-yl)acetamide. NMR; δH [$^2$H$_6$]—DMSO 9.92,(1H, s), 8.60,(1H, t), 7.91,(2H, d), 7.48-7.47,(2H, m), 7.39,(2H, d), 7.21,(1H, d), 3.16,(2H, t), 2.15, (3H, s), 2.01,(3H, s), 1.04,(1H, m), 0.43,(2H, m), 0.24,(2H, m). LCMS: retention time 2.86 min, MH$^+$323.

Example 61

N-(4'-{[(Cyclopropylmethyl)amino]carbonyl}-6-methyl-1,1'-biphenyl-3-yl)isovaleramide 5'-Amino-N-(cyclopropylmethyl)-2'-methyl-1,1'-biphenyl-4-carboxamide (30 mg, 0.11 mmol) and isovaleric acid (25.5 mg, 0.25 mmol) were mixed in THF (3 ml). Carbodiimde resin (295 mg, 0.31 mmol) was added and shaking continued for 72 h. The reaction was filtered, the resin washed with THF and methanol and the combined filtrate and washings filtered through an SPE (SCX), to give, after evaporation of the solvent under vacuum, N-(4'-{[(cyclopropylmethyl)amino]carbonyl}-6-methyl-1,1'-biphenyl-3-yl)isovaleramide. NMR; δH [$^2$H$_6$]—DMSO 9.84,(1H, s), 8.60,(1H, t), 7.91, (2H, d), 7.50-7.48,(2H, m), 7.40,(2H, d), 7.21,(1H, d), 3.16, (2H, t), 2.16-2.15,(5H, m), 2.06,(1H, m), 1.04,(1H, m), 0.91, (6H, d), 0.43,(2H, m), 0.24,(2H, m). LCMS: retention time 3.25 min, MH$^+$365.

Example 62

N-(4'-{[(Cyclopropylmethyl)amino]carbonyl}-6-methyl-1,1'-biphenyl-3-yl)trifluoroacetamide 5'-Amino-N-(cyclopropylmethyl)-2'-methyl-1,1'-biphenyl-4-carboxamide (30 mg, 0.11 mmol) and trifluoroacetic acid (28.5 mg, 0.25 mmol) were mixed in THF (3 ml). Carbodiimde resin (295 mg, 0.31 mmol) was added and shaking continued for 72 h. The reaction was filtered, the resin washed with THF and methanol and the combined filtrate and washings filtered through an SPE (SCX), to give, after evaporation of the solvent under vacuum, N-(4'-{[(cyclopropylmethyl) amino]carbonyl}-6-methyl-1,1'-biphenyl-3-yl)trifluoroacetamide. NMR; δH [$^2$H$_6$]—DMSO 11.25,(1H, s), 8.62,(1H, t), 7.92,(2H, d), 7.60,(1H, dd), 7.55,(1H, d), 7.43,(2H, d), 7.34, (1H, d), 3.16,(2H, t), 2.21,(3H, s), 1.04,(1H, m), 0.43,(2H, m), 0.24,(2H, m). LCMS: retention time 3.29 min, MH$^+$377.

Example 63

N-(4'-{[(Cyclopropylmethyl)amino]carbonyl}-6-methyl-1,1'-biphenyl-3-yl)-6-(4-fluorophenyl)pyrazine-2-carboxamide 5'-Amino-N-(cyclopropylmethyl)-2'-methyl-1,1'-biphenyl4-carboxamide (75 mg, 0.27 mmol), 6-(4fluorophenyl) pyrazine-2-carboxylic acid (58.4 mg, 0.27 mmol), HATU (101.5 mg, 0.27 mmol), HOBT (36 mg, 0.27 mmol) and DIPEA (140 μl, 0.80 mmol) in DMF (3 ml) were stirred at room temperature for 18 h. The reaction was diluted with ethyl acetate (150 ml), washed with hydrochloric acid (0.5M, 2×20ml), aqueous sodium hydrogen carbonate (20 ml) and dried (magnesium sulphate). Evaporation of the solvents under vacuum gave N-(4'-{[(cyclopropylmethyl)amino]carbonyl}-6-methyl-1,1'-biphenyl-3-yl)-6-(4-fluorophenyl) pyrazine-2-carboxamide (117 mg, 91%). NMR; δH [$^2$H$_6$]—DMSO 10:64,(1H, s), 9.52,(1H, s), 9.20,(1H, s), 8.63,(1H, t), 8.54,(2H, m), 7.95,(2H, d), 7.88,(1H, dd), 7.78,(1H, d), 7.48, (2H, d), 7.42,(2H, t), 7.35,(1H, d), 3.17,(2H, t), 2.23,(3H, s), 1.05,(1H, m), 0.24,(2H, m). LCMS: retention time 3.65 min, MH$^+$481.

Example 64

N-(4'-{[(Cyclopropylmethyl)amino]carbonyl}-6-methyl-1,1'-biphenyl-3-yl)-6-morpholin-4-ylpyrazine-2-carboxamide 5'-Amino-N-(cyclopropylmethyl)-2'-methyl-1,1'-biphenyl-4carboxamide (75 mg, 0.27 mmol), 6-morpholin-4-ylpyrazine-2-carboxylic acid (55.9 mg, 0.27 mmol), HATU (101.5 mg, 0.27 mmol), HOBT (36 mg, 0.27 mmol) and DIPEA (140 μl, 0.80 mmol) in DMF (3 ml) were stirred at room temperature for 18 h. The reaction was diluted with ethyl acetate (150 ml), washed with hydrochloric acid (0.5M, 2×20 ml), aqueous sodium hydrogen carbonate (20 ml) and dried (magnesium sulphate). Evaporation of the solvents under vacuum gave N-(4'-{[(cyclopropylmethyl)amino]carbonyl}-6-methyl-1,1'-biphenyl-3-yl)-6-morpholin-4-ylpyrazine-2-carboxamide (118 mg, 94%). NMR; δH [$^2$H$_6$]—DMSO 10.17,(1H, s), 8.62,(1H, t), 8.54,(1H, s), 8.47,(1H, s), 7.93,(2H, d), 7.80,(1H, dd), 7.70,(1H, d), 7.45,(2H, d), 7.31, (1H, d), 3.73,(8H, m), 3.16,(2H, t), 2.21,(3H, s), 1.04,(1H, m), 0.43,(2H, m), 0.24,(2H, m). LCMS: retention time 3.20 min, MH$^+$472.

Example 65

N-(4'-{[(3-Dimethylaminopropyl)amino]carbonyl}-6-methyl-1,1'-biphenyl-3-yl)-3-furamide a) 5'-(3-Furoylamino)-2'-methyl-1,1'-biphenyl-4-carboxylic acid (50 mg, 0.156 mmol), 3-dimethylaminopropylamine (15.9 mg, 0.156 mmol), HATU (59.2 mg, 0.156 mmol), HOBT (21 mg, 0.156 mmol) and DIPEA (27 μl, 0.30 mmol) in DMF (2 ml) were stirred at room temperature for 18 h. The reaction was diluted with ethyl acetate (150 ml), washed with water (2×30 ml) and dried (magnesium sulphate). The solvent was evaporated under vacuum and the residue chromatographed on a silica flash column eluting with DCM/methanol/triethylamine (96:2:2). Concentration of the product fractions under vacuum gave N-(4'-{[(3-dimethylaminopropyl)amino]carbonyl}-6-methyl-1,1'-biphenyl-3-yl)-3-furamide (51 mg, 81%). NMR; δH [$^2$H$_6$]—DMSO 9.92,(1H, s), 8.61,(1H, t), 8.35,(1H, d), 7.91,(2H, d), 7.78,(1H, t), 7.64,(1H, dd), 7.61,(1H, d), 7.44,(2H, d), 7.27,(1H, d), 6.98,(1H, m), 2.94,(2H, b), 2.58,(2H, b), 2.38,(6H, s), 2.19,(3H, s), 1.76,(2H, m). LCMS: retention time 2.23 min, MH$^+$406.

b) 5'-(3-Furoylamino)-2'-methyl-1,1'-biphenyl-4-carboxylic acid Methyl 5'-(3-furoylamino)-2'-methyl-1,1'-biphenyl-4-carboxylate (980 mg, 2.9 mmol) and lithium hydroxide monohydrate (256 mg, 6.1 mmol) in THF (12 ml) and water (6 ml) were heated at 75° C. for 18 h. The THF was evaporated under vacuum and the aqueous adjusted to pH3 with hydrochloric acid (1M). The precipitate which formed was filtered off, washed with ether and dried under vacuum to give 5'-(3-furoylamino)-2'-methyl-1,1'-biphenyl-4-carboxylic acid (720 mg, 77%). LCMS: retention time 3.33 min, MH$^+$322.

c) Methyl 5'-(3-furoylamino)-2'-methyl-1,1'-biphenyl-4-carboxylate 3-Furoic acid (557 mg, 4.97 mmol), HATU (1.89 g, 4.97 mmol), HBTU (560 mg, 4.14 mmol), methyl 5'-amino-2'-methyl-1,1'-biphenyl-4-carboxylate (1.0 g, 4.14 mmol) and DIPEA (2.17 ml, 12.43 mmol) were mixed in DMF (5 ml) and the reaction stirred at room temperature for 18 h. The DMF was evaporated under vacuum, the residue partitioned between DCM (50 ml) and aqueous sodium carbonate (1M, 50 ml) and the aqueous extracted with DCM (2×30 ml). The combined organics were washed with brine (75 ml), dried (magnesium sulphate) and concentrated under vacuum. The residue was purified on a silica flash column eluting with DCM/ethanol/ammonia (500:8:1), which after evaporation of the solvents under vacuum gave methyl 5'-(3-furoylamino)-2'-methyl-1,1'-biphenyl-4-carboxylate (800 mg, 58%). LCMS: retention time 3.41 min, MH$^+$336.

Example 66

N-[6-Methyl-4'-({[2-(methylsulphonylamino)ethyl]amino}carbonyl)-1,1'-biphenyl-3-yl]-3-furamide 5'-(3-Furoylamino)-2'-methyl-1,1'-biphenyl-4-carboxylic acid (30 mg, 0.093 mmol), N-(2-aminoethyl)methylsulphonamide (12.9 mg, 0.093 mmol), HATU (35.5 mg, 0.093 mmol), HOBT (12.6 mg, 0.093 mmol) and DIPEA (481 μl, 0.28 mmol) in DMF (2 ml) were stirred at room temperature for 18 h. The reaction was diluted with ethyl acetate (150 ml), washed with water (2×30ml) and dried (magnesium sulphate). The solvent was evaporated under vacuum and the residue chromatographed on a silica flash column eluting with DCM/methanol/triethylamine (96:2:2). Concentration of the product fractions under vacuum gave N-[6-methyl-4'-({[2-(methylsulphonylamino)ethyl]amino}carbonyl)-1,1'-biphenyl-3-yl]-3-furamide (37 mg, 90%). NMR; δH [$^2$H$_6$]—DMSO 9.91,(1H, s), 8.59,(1H, t), 8.35,(1H, s), 7.92,(2H, d), 7.78,(1H, t), 7.66,(1H, dd), 7.59,(1H, d), 7.45,(2H, d), 7.27, (1H, d), 7.17,(1H, t), 6.98,(1H, m), 3.40,(2H, q), 3.13,(2H, q), 2.91,(3H, s), 2.19,(3H, s). LCMS: retention time 2.82 min, MH$^+$442.

Example 67

N-(4'-{[(2-Hydroxyethyl)amino]carbonyl}-6-methyl-1,1'-biphenyl-3-yl)-3-furamide 5'-(3-Furoylamino)-2'-methyl-1,1'-biphenyl-4-carboxylic acid (30 mg, 0.093 mmol), 2-hydroxyethylamine (5.7 mg, 0.093 mmol), HATU (35.5 mg, 0.093 mmol), HOBT (12.6 mg, 0.093 mmol) and DIPEA (48 µl, 0.28 mmol) in DMF (2 ml) were stirred at room temperature for 18 h. The reaction was diluted with ethyl acetate (150 ml), washed with water (2×30 ml) and dried (magnesium sulphate). The solvent was evaporated under vacuum and the residue chromatographed on a silica flash column eluting with DCM/methanol/triethylamine (96:2:2). Concentration of the product fractions under vacuum gave N-(4'-{[(2-hydroxyethyl)amino]carbonyl}-6-methyl-1,1'-biphenyl-3-yl)-3-furamide (31.2 mg, 92%). NMR; δH [$^2$H$_6$]—DMSO 9.91,(1H, s), 8.49,(1H, t), 8.35,(1H, s), 7.92,(2H, d), 7.78,(1H, t), 7.67,(1H, dd), 7.59,(1H, d), 7.43,(2H, d), 7.27,(1H, d), 6.97,(1H, m), 4.73,(1H, t), 3.52, (2H, q), 3.35,(2H, m), 2.19,(3H, s). LCMS: retention time 2.72 min, MH$^+$365.

Example 68

N-(4'-{[(3-Hydroxypropyl)amino]carbonyl}-6-methyl-1,1'-biphenyl-3-yl)-3-furamide 5'-(3-Furoylamino)-2'-methyl-1,1'-biphenyl-4-carboxylic acid (30 mg, 0.093 mmol), 3-hydroxypropylamine (7 mg, 0.093 mmol), HATU (35.5 mg, 0.093 mmol), HOBT (12.6 mg, 0.093 mmol) and DIPEA (48 µl, 0.28 mmol) in DMF (2 ml) were stirred at room temperature for 18 h. The reaction was diluted with ethyl acetate (150 ml), washed with water (2×30 ml) and dried (magnesium sulphate). The solvent was evaporated under vacuum and the residue chromatographed on a silica flash column eluting with DCM/methanol/triethylamine (96:2:2). Concentration of the product fractions under vacuum gave N-(4'-{[(3-hydroxypropyl)amino]carbonyl}-6-methyl-1,1'-biphenyl-3-yl)-3-furamide (29.4 mg, 83%). NMR; δH [$^2$H$_6$]—DMSO 9.91,(1H, s), 8.50,(1H, t), 8.35, (1H, s), 7.90,(2H, d), 7.78,(1H, t), 7.66,(1H, dd), 7.59,(1H, d), 7.43,(2H, d), 7.27,(1H, d), 6.97,(1H, m), 4.49,(1H, t), 3.47, (2H, q), 3.33,(2H, m), 2.19,(3H, s), 1.69,(2H, m). LCMS: retention time 2.77 min, MH$^+$379.

Example 69

N-(4'-{[(Cyclopropylmethyl)amino]carbonyl}-6-methyl-1,1'-biphenyl-3-yl)thiophene-2-carboxamide 5'-Amino-N-(cyclopropylmethyl)-2'-methyl-1,1'-biphenylcarboxamide (42 mg, 0.15 mmol) and thiophene-2-carboxylic acid (0.40 mmol) were mixed in THF (5 ml). Carbodiimde resin (495 mg, 0.5 mmol) was added and shaking continued for 18 h. The reaction was filtered, the resin washed with THF and methanol and the combined filtrate and washings filtered through an SPE (SCX). The filtrate was purified by chromatography on a silica SPE to give, after evaporation of the solvent under vacuum, N-(4'-{[(cyclopropylmethyl)amino]carbonyl}6-methyl-1,1'-biphenyl-3-yl)thiophene-2-carboxamide. NMR; δH [$^2$H$_6$]—DMSO 10.24,(1H, s), 8.63, (1H, t), 8.02,(1H, dd), 7.94,(2H, d), 7.86,(1H, dd), 7.69,(1H, dd), 7.63,(1H, d), 7.46,(2H, d), 7.30,(1H, d), 7.22,(1H, m), 3.18,(2H, t), 2.21,(3H, s), 1.06,(1H, m), 0.45,(2H, m), 0.25, (2H, m). LCMS: retention time 3.36 min, MH$^+$391.

Example 70

N-(4'-{[(Cyclopropylmethyl)amino]carbonyl}-6-methyl-1,1'-biphenyl-3-yl)benzamide 5'-Amino-N-(cyclopropylmethyl)-2'-methyl-1,1'-biphenyl-4-carboxamide (42 mg, 0.15 mmol) and benzoic acid (0.40 mmol) were mixed in THF (5 ml). Carbodiimde resin (495 mg, 0.5 mmol) was added and shaking continued for 18 h. The reaction was filtered, the resin washed with THF and methanol and the combined filtrate and washings filtered through an SPE (SCX) to give, after evaporation of the solvent under vacuum, N-(4'-{[(cyclopropylmethyl)amino]carbonyl}-6-methyl-1,1'-biphenyl-3-yl)benzamide. NMR; δH [$^2$H$_6$]—DMSO 10.25,(1H, s), 8.62,(1H, t), 7.95-7.92,(4H, m), 7.73,(1H, dd), 7.69,(1H, d), 7.60-7.50,(3H, m), 7.44,(2H, d), 7.28,(1H, d), 3.16,(2H, t), 2.20,(3H, s), 1.04,(1H, m), 0.43,(2H, m), 0.24,(2H, m). LCMS: retention time 3.41 min, MH$^+$385.

Example 71

N-(4'-{[(Cyclopropylmethyl)amino]carbonyl}-6-methyl-1,1'-biphenyl-3-yl)-5-(3-chlorophenyl)-2-furamide 5'-Amino-N-(cyclopropylmethyl)-2'-methyl-1,1'-biphenyl-4-carboxamide (24 mg, 0.085 mmol), 5-(3-chlorophenyl)-2-furoic acid (9.5 mg, 0.043 mmol), 1-(3-dimethylaminopropyl)-3-ethylcarbodiimide hydrochloride (16 mg, 0.085 mmol), HOBT (12 mg, 0.085 mmol) and DIPEA (15 µl, 0.085 mmol) in DMF (4 ml) were stirred at room temperature for 4 h. The DMF was evaporated under vacuum and the residue partitioned between ethyl acetate and water. The organic fraction was concentrated under vacuum and the residue purfied by preparative HPLC to give N-(4'-{[(cyclopropylmethyl)amino]carbonyl}-6-methyl-1,1'-biphenyl-3-yl)-5-(3-chlorophenyl)-2-furamide (20 mg, 95%). NMR; δH [$^2$H$_6$]—DMSO 10.25,(1H, s), 8.64,(1H, t), 8.11,(1H, t), 7.96-7.94, (3H, m), 7.75,(1H, dd), 7.66,(1H, d), 7.52,(1H, t), 7.49-7.44, (3H, m), 7.39,(1H, d), 7.34-7.31,(2H, m), 3.18,(2H, t), 2.23, (3H, s), 1.06,(1H, m), 0.45,(2H, m), 0.26,(2H, m). LCMS: retention time 3.88 min, MH$^+$485.

Example 72

N-(6-Chloro-4'-{[(cyclopropylmethyl)amino]carbonyl}-1,1'-biphenyl-3-yl)-3-furamide N-(3-Bromo-4-chlorophenyl)-3-furamide (Intermediate 1, 63 mg), N-cyclopropylmethyl-4-(4,4,5,5-tetramethyl-[1,3,2] dioxaborolan-2-yl)benzamide (60 mg), tetrakis(triphenylphosphine) palladium (5 mg) and aqueous sodium carbonate (2N, 0.5 ml) were mixed in DMF (1.2 ml) and heated at 80° C. under nitrogen for 18 hrs. The cooled reaction was absorbed onto silica, applied to an SPE (Si) and eluted with an ethyl acetate/cyclohexane gradient (0-100% ethyl acetate). The product fractions were reduced to dryness under vacuum and triturated with ether to give N-(6-chloro-4'-{[(cyclopropylmethyl)amino]carbonyl}-1,1'-biphenyl-3-yl)-3-furamide. NMR; δH [$^2$H$_6$]—DMSO 10.10,(1H, s), 8.65,(1H, t), 8.38,(1H, s), 7.94,(2H, d), 7.80,(3H, m), 7.54,(3H, m), 6.98, (1H, s), 3.16,(2H, t), 1.06,(1H, m), 0.43,(2H, m), 0.24,(2H, m). LCMS MH$^+$395/397, retention time 3.32 minutes.

(a) N-(3-Bromo-4-chlorophenyl)-3-furamide (Intermediate 1)

3-Bromo-4-chloroaniline (150 mg), 3-furoylchloride (0.15 ml) and sodium carbonate (1 g) were stirred for 18 hours at room temperature in DCM (15 ml). The reaction was filtered, the residue washed with DCM and the combined DCM fractions reduced to dryness under vacuum to give N-(3-bromo-4-chlorophenyl)-3-furamide. NMR; δH [$^2$H$_6$]—DMSO 10.13,(1H, s), 8.38,(1H, s), 8.20,(1H, d), 7.81,(1H, m), 7.73, (1H, dd), 7.59,(1H, d), 6.97,(1H, m).

Example 73

N-(4'-{[(4-Hydroxybutyl)amino]carbonyl}-6-methyl-1,1'-biphenyl-3-yl)-3-furamide To a solution of [3'-(3-furoylamino)-6'-methyl-1,1'-biphen-4-yl]carboxylic acid (75 mg), HATU (89 mg) and HOBT (32 mg) in DMF (2.25 ml) was added DIPEA (0.122 ml) and 4-hydroxybutylamine (0.022 ml) and the mixture stirred for 18 hours at room temperature. The reaction was partitioned between ethyl acetate and hydrochloric acid (0.5M, 20 ml), the organic phase washed with hydrochloric acid (0.5M, 20 ml), saturated sodiumhydrogen carbonate solution (2×20ml) and water (2×20ml), dried (magnesium sulphate) and the solvent evaporated under vacuum to give N-(4'-{[(4-hydroxybutyl)amino]carbonyl}-6-methyl-1,1'-biphenyl-3-yl)-3-furamide (86.9 mg). NMR; δH [$^2$H$_6$]—DMSO 9.91,(1H, s), 8.51,(1H, b), 8.35,(1H, s), 7.92-7.89, (2H, m), 7.78,(1H, m), 7.66,(1H, d), 7.59,(1H, s), 7.43,(2H, m), 7.27,(1H, m), 6.98,(1H, s), 4.42,(1H, m), 3.42,(2H, m), 3.28,(2H, m), 2.19,(3H, s), 1.58-1.44,(4H, m). LCMS: MH$^+$393, retention time 2.90 minutes.

Example 74

N-(4'-{[(4-Hydroxybutyl)amino]carbonyl}-6-methyl-1,1'-biphenyl-3-yl)thiophene-3-carboxamide

Example 75

N-(4'-{[(3-Hydroxypropyl)amino]carbonyl}-6-methyl-1,1'-biphenyl-3-yl)thiophene-3-carboxamide

Example 76

N-(4'-{[(2-Hydroxyethyl)amino]carbonyl}-6-methyl-1,1'biphenyl-3-yl)thiophene-3-carboxamide

Example 77

N-[4'-{[3-(Dimethylamino)-2,2-dimethylpropyl]amino}carbonyl)-6-methyl-1,1'-biphenyl-3-yl]thiophene-3-carboxamide

Example 78

N-{6-Methyl-4'-[({2-[(methylsulfonyl)amino]ethyl}amino)carbonyl]-1,1'-biphenyl-3-yl}thiophene-3-carboxamide

Example 79

N-[4'-({[3-(Dimethylamino)propyl]amino}carbonyl)-6-methyl-1,1'-biphenyl-3-yl]thiophene-3-carboxamide

General Method F

{3'-[(3-Thiophenylcarbonyl)amino]-6'-methyl-1,1'-biphen-4-yl}carboxylic acid (Intermediate 2, 0.06 mmol), triethylamine (13 ul) and 1-(methylsulphonyl)-1H-benzotriazole (12 mg, 0.06 mmol) were mixed in THF (0.5 ml) and heated at reflux for 4 hours. The reaction was concentrated under vacuum and partitioned between chloroform (3 ml) and water (2 ml) and the organics reduced to dryness under vacuum. The residue was redissolved in THF (0.5 ml) and was mixed with the amine (0.06 mmol). After 20 hours the reaction was loaded onto an SPE (aminopropyl, 0.5 g) and eluted with chloroform to give the desired product.

| Compound | Amine | MH$^+$ | Retention time (minutes) |
|---|---|---|---|
| Example 74 | 4-hydroxybutylamine | 409 | 2.90 |
| Example 75 | 3-hydroxypropylamine | 395 | 2.88 |
| Example 76 | 2-hydroxyethylamine | 381 | 2.82 |
| Example 77 | 3-(N,N-dimethylamino)-2,2-dimethylpropylamine | 450 | 2.49 |
| Example 78 | N-(2-aminoethyl)methanesulphonamide | 458 | 2.92 |
| Example 79 | 3-(N,N-dimethylamino)propylamine | 422 | 2.40 |

(a) {3'-[(3-Thiophenylcarbonyl)amino]-6'-methyl-1,1'-biphen-4-yl}carboxylic acid (Intermediate 2)

A solution of lithium hydroxide monohydrate (541 mg, 12.9 mmol) in water (8 ml) was added to a solution of methyl {3'-[(3-thiophenylcarbonyl)amino]-6'-methyl-1,1'-biphen-4-yl}carboxylate (Intermediate 3, 1.37 g, 4.3 mmol) in THF (10 ml). The reaction was refluxed for 4 hours. Solvent was evaporated in vacuo, hydrochloric acid (0.5M,50 ml) was added and the product was extracted into ethyl acetate (2×50 ml). The solvent was evaporated in vacuo to afford {3'-[(3-thiophenylcarbonyl)amino]-6'-methyl-1,1'-biphen-4-yl}carboxylic acid (1.68 g, 98%).

NMR: δH [$^2$H$_6$]—DMSO 13.10,(1 H, bs), 8.33,(1H, dd), 8.03,(2H, d), 7.72,(1 H, dd), 7.68-7.60,(3H, m) 7.50,(2H, d), 7.30,(1H, d), 2.20,(3H, s). LCMS: MH$^+$338, retention time 3.47 minutes.

(b) Methyl {3'-[(3-thiophenylcarbonyl)amino]-6'-methyl-1,1'-biphenyl}carboxylate (Intermediate 3)

Methyl (3'-amino-6'-methyl-1,1'-biphenyl)carboxylate (1.45 g, 6.0 mmol), thiophene-3-carboxylic acid (0.846 g, 6.6 mmol), HOBT (0.973 g, 7.2 mmol) and 1-(3-dimethylaminopropyl)-3-ethylcarbodiimide hydrochloride (1.38 g, 7.2 mmol) were dissolved in DMF (10 ml). DIPEA (1.26 ml, 7.2 mmol) was added to the stirred solution, which was then stirred for 16 hours at 20° C. The solvent was removed in vacuo and the residue dissolved in ethyl acetate. The ethyl acetate solution was washed sequentially with aqueous sodium hydrogen carbonate (80 ml) and hydrochloric acid (0.5M, 80 ml), then dried (magnesium sulphate). The solvent was removed in vacuo and the residue was purified by silica biotage chromatography eluting with 4:1 cyclohexane:ethyl acetate. To give methyl {3'-[(3-thiophenylcarbonyl)amino]-6'-methyl-1,1'-biphen-4-yl}carboxylate (1.78 g, 84%).

NMR: δH [$^2$H$_6$]—DMSO 10.1,(1H, s), 8.33,(1H, m), 8.05, (2H, d), 7.72,(1H, dd), 7.70-7.60,(3H, m) 7.52,(2H, d), 7.30, (1H, d), 3.89,(3H, s), 2.20,(3H, s). LCMS: MH$^+$352, retention time 3.64 minutes.

Abbreviations

| | |
|---|---|
| DCM | Dichloromethane |
| DIPEA | N,N-Diisopropylethylamine |
| DME | Dimethoxyethane |
| DMF | Dimethylformamide |
| DMSO | Dimethylsulphoxide |
| HATU | O-(7-Azabenzotriazol-1-yl)-N,N,N',N'-tetramethyluronium hexafluorophosphate |
| HBTU | O-Benzotriazol-1-yl-N,N,N',N'-tetramethyluronium hexafluorophosphate |
| HOBT | 1-Hydroxybenzotriazole hydrate |
| PyBOP | Benzotriazol-1-yl-oxy-tripyrrolidinophosphonium hexafluorophosphate |
| SPF | Solid phase extraction |
| THF | Tetrahydrofuran |

The activity of the compounds of the invention as p38 inhibitors may be demonstrated in the following assays:

p38 Kinase Assay

The peptide substrate used in the p38 assay was biotin-IPTSPITTTYFFFRRR-amide. The p38 and MEK6 proteins were purified to homogeneity from E. coli expression systems. The fusion proteins were tagged at the N-terminus with Glutathione-S-Transferase (GST). The maximum activation was achieved by incubating 20 uL of a reaction mixture of 30 nM MEK6 protein and 120 nM p38 protein in the presence of 1.5 uM peptide and 10 mM $Mg(CH_3CO_2)_2$ in 100 mM HEPES, pH 7.5, added to 15 uL of a mixture of 1.5 uM ATP with 0.08 uCi [g-$^{33}$P]ATP, with or without 15 uL of inhibitor in 6% DMSO. The controls were reactions in the presence (negative controls) or absence (positive controls) of 50 mM EDTA. Reactions were allowed to proceed for 60 min at room temperature and quenched with addition of 50 uL of 250 mM EDTA and mixed with 150uL of Streptavidin SPA beads (Amersham) to 0.5 mg/reaction. The Dynatech Microfluor white U-bottom plates were sealed and the beads were allowed to settle overnight. The plates were counted in a Packard TopCount for 60 seconds. $IC_{50}$ values were obtained by fitting raw data to % I=100*(1-(I-C2)/(C1-C2)), where I was CPM of background, C1 was positive control, and C2 was negative control.

αP38 Fluorescence Polarisation Method

αP38 was prepared in house. SB4777790-R Ligand was diluted in HEPES containing $MgCl_2$, CHAPS, DTT and DMSO. This was added to blank wells of a Black NUNC 384 well plate. αP38 was added to this ligand mixture then added to the remainder of the 384 well plate containing controls and compounds. The plates were read on an LJL Analyst and Fluorescence Anisotropy used to calculate the compound inhibition The application of which this description and claims forms part may be used as a basis for priority in respect of any subsequent application. The claims of such subsequent application may be directed to any feature or combination of features described herein. They may take the form of product, composition, process or use claims and may include, by way of example and without limitation, one or more of the following claims:

The invention claimed is:
1. A compound of formula (I):

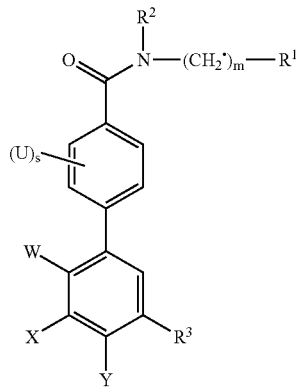

(I)

wherein
when m is 0 to 4, $R^1$ is selected from $C_{1-6}$alkyl, $C_{3-7}$cycloalkyl, $C_{2-6}$alkenyl, —$SO_2NR^4R^5$, —$CONR^4R^5$ and —$COOR^4$;

and when m is 2 to 4, $R^1$ is additionally selected from $C_{1-6}$alkoxy, hydroxy, $NR^4R^5$, —$NR^4SO_2R^5$, —$NR^4SOR^5$, —$NR^4COR^5$, and —$NR^4CONR^4R^5$; provided that when $R^1$ is $NR^4R^5$ then $R^4$ and $R^5$ do not cyclize to form a five-to six-membered heterocyclic or heteroaryl ring;

$R^2$ is selected from hydrogen, $C_{1-6}$alkyl and —$(CH_2)_n$—$C_{3-7}$cycloalkyl;

$R^3$ is the group —NH—CO—$R^6$;

$R^4$ and $R^5$ are independently selected from hydrogen, $C_{1-6}$alkyl, heterocyclyl optionally substituted by $C_{1-4}$alkyl, and phenyl wherein the phenyl is optionally substituted by up to two groups independently selected from $C_{1-6}$alkoxy, $C_{1-6}$alkyl and halogen;

or $R^4$ and $R^5$, together with the nitrogen atom to which they are bound, form a five-to six-membered heterocyclic or heteroaryl ring optionally containing one additional heteroatom selected from oxygen, sulfur and nitrogen, wherein the ring may be substituted by up to two $C_{1-6}$alkyl groups;

$R^6$ is selected from hydrogen, $C_{1-6}$alkyl, $C_{1-6}$alkoxy, —$(CH_2)_p$—$C_{3-7}$cycloalkyl, trifluoromethyl, —$(CH_2)_q$ phenyl optionally substituted by $R^7$ and/or $R^8$, —$(CH_2)_q$ heteroaryl optionally substituted by $R^7$ and/or $R^8$, —$(CH_2)_q$heterocyclyl optionally substituted by $R^7$ and/or $R^8$ and —$(CH_2)_q$fused bicyclyl optionally substituted by $R^7$ and/or $R^8$;

$R^7$ is selected from $C_{1-6}$alkyl, $C_{1-6}$alkoxy, —$(CH_2)_p$—$C_{3-7}$ cycloalkyl, —$CONR^9R^{10}$, —$NHCOR^{10}$, —$SO_2NHR^9$, —$NHSO_2R^{10}$, halogen, —$(CH_2)_r$ $NR^{11}R^{12}$, oxy, trifluoromethyl, phenyl optionally substituted by one or more $R^8$ groups and heteroaryl wherein the heteroaryl may be optionally substituted by one or more $R^8$ groups;

$R^8$ is selected from $C_{1-6}$alkyl, $C_{1-6}$alkoxy, halogen, trifluoromethyl and —$NR^{11}R^{12}$;

or $R^7$ and $R^8$, together with the carbon atoms to which they are bound, form a five-or six-membered saturated or unsaturated ring to give a fused bicyclic ring system, wherein the ring that is formed by $R^7$ and $R^8$ may optionally contain one or two heteroatoms selected from oxygen, nitrogen and sulfur;

$R_9$ is selected from hydrogen, $C_{1-6}$alkyl and phenyl wherein the phenyl group may be optionally substituted by one or more $R^8$ groups;

$R^{10}$ is selected from hydrogen and $C_{1-6}$alkyl;

or $R^9$ and $R^{10}$, together with the nitrogen atom to which they are bound, form a five-to six-membered heterocyclic ring optionally containing one additional heteroatom selected from oxygen, sulfur and nitrogen, wherein the ring may be substituted by up to two $C_{1-6}$alkyl groups;

$R^x$ is selected from hydrogen and methyl;

$R^{11}$ is selected from hydrogen, $C_{1-6}$alkyl and —$(CH_2)_p$—$C_{3-7}$cycloalkyl optionally substituted by $C_{1-6}$alkyl;

$R^{12}$ is selected from hydrogen and $C_{1-6}$alkyl;

or $R^{11}$ and $R^{12}$, together with the nitrogen atom to which they are bound, form a three- to seven-membered heterocyclic ring optionally containing up to one additional heteroatom selected from oxygen, sulfur and N—$R^x$, wherein the ring may contain up to one double bond and the ring may be substituted by one or more $R^{13}$ groups;

$R^{13}$ is selected from $C_{1-6}$alkyl, oxy, —$CH_2OC_{1-6}$alkyl, trichloromethyl and —$N(C_{1-6}$alkyl$)_2$;

U is selected from methyl and halogen;

W is selected from methyl and chlorine;

X and Y are each selected independently from hydrogen, methyl and halogen;

m is selected from 0, 1, 2, 3 and 4 wherein each carbon atom of the resulting carbon chain may be optionally substituted with one or two groups selected independently from $C_{1-6}$alkyl optionally substituted by up to three halogens;

n, p and q are independently selected from 0 and 1;

r is selected from 0, 1, 2 and 3;

s is selected from 0, 1 and 2;

or a pharmaceutically acceptable salt or solvate thereof.

2. A compound according to claim 1 wherein $R^1$ is selected from $C_{1-4}$alkyl, $C_{3-6}$cycloalkyl, —$CONHCH_3$, —$SO_2NH_2$, —$SO_2N(CH_3)_2$, methoxy, —$NHSO_2CH_3$ and —$NHCOCH_3$.

3. A compound according to claim 1 wherein $R^1$ is selected from $C_{3-6}$cycloalkyl, hydroxy, $NR^4R^5$, and —$NR^4SO_2R^5$.

4. A compound according to claim 1 wherein $R^2$ is selected from hydrogen, $C_{1-4}$alkyl and —$CH_2$-cyclopropyl.

5. A compound according to claim 4 wherein $R^2$ is hydrogen.

6. A compound according to claim 1 wherein $R^6$ is selected from —$(CH_2)_r$phenyl optionally substituted by $R^7$ and/or $R^8$ and —$(CH_2)_r$heteroaryl optionally substituted by $R^7$ and/or $R^8$.

7. A compound according to any one of claim 1 wherein $R^6$ is selected from $C_{1-4}$alkyl, —$(CH_2)_p$—$C_{3-6}$cycloalkyl, trifluoromethyl, —$(CH_2)_q$phenyl optionally substituted by $R^7$ and/or $R^8$, —$(CH_2)_q$heteroaryl optionally substituted by $R^7$ and/or $R^8$, —$(CH_2)_q$heterocyclyl optionally substituted by $R^7$ and/or $R^8$ and —$(CH_2)_q$fused bicyclyl optionally substituted by $R^7$ and/or $R^8$.

8. A compound according to claim 1 wherein q is 0.

9. A compound according to claim 1 wherein m is selected from 0, 1 and 2.

10. A process for preparing a compound according to any one of claims 1 to 9 which comprises:

(a) reacting a compound of formula (XI)

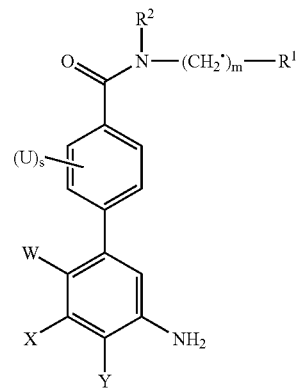

(XI)

wherein $R^1$, $R^2$, U, W, X, Y, m and s are as defined in any one of claims 1 to 9 with a compound of formula (XII)

$$R^6CO_2H \quad (XII)$$

wherein $R^6$ is as defined in any one of claims 1 to 9 under amide forming conditions, optionally converting the acid compound (XII) to an activated form of the acid before reaction with the amine compound (XI); or (b) reacting a compound of formula (XIII)

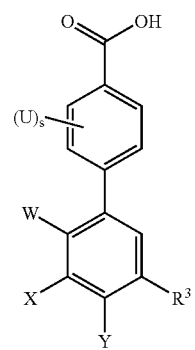

(XIII)

wherein $R^3$, U, W, X, Y and s are as defined in any one of claims 1 to 9 with a compound of formula (XIV)

$$R^1(CH_2)_mNR_2H \quad (XIV)$$

wherein $R^1$, $R^2$ and m are as defined in any one of claims 1 to 9 under amide forming conditions.

11. A pharmaceutical composition comprising a compound according to claim 1 or a pharmaceutically acceptable salt or solvate thereof, in admixture with one or more pharmaceutically acceptable carriers, diluents or excipients.

12. A compound according to claim 1 which is:

N-(4'-{[(Cyclopropylmethyl)amino]carbonyl}-6-methyl-1,1'-biphenyl-3-yl)nicotinamide;

4-Chloro-N-(4'-{[(cyclopropylmethyl)amino]carbonyl}-6-methyl-1,1'-biphenyl-3-yl)benzamide;

N-(4'-{[(Cyclopropylmethyl)amino]carbonyl}-6-methyl-1,1'-biphenyl-3-yl)-4-methylbenzamide;

2-Amino-N-(4'-{[(cyclopropylmethyl)amino]carbonyl}-6-methyl-1,1'-biphenyl-3-yl )isonicotinamide;

N-(4'-{[(Cyclopropylmethyl)amino]carbonyl}-6-methyl-1,1'-biphenyl-3-yl)-3-furamide;

2-Chloro-N-(4'-{[(cyclopropylmethyl)amino]carbonyl}-6-methyl-1,1'-biphenyl-3-yl-isonicotinamide;

N-(4'-{[(Cyclopropylmethyl)amino]carbonyl}-6-methyl-1,1'-biphenyl-3-yl)-2-piperidin-1-yl-quinoline-4-carboxamide;

N-(4'-{[(Cyclopropylmethyl)amino]carbonyl}-6-methyl-1,1'-biphenyl-3-yl)-2-pyrrolidin-1-yl-isonicotinamide;

N-(4'-{[(Cyclopropylmethyl)amino]carbonyl}-6-methyl-1,1'-biphenyl-3-yl)-2-(4-methylpiperazin-1-yl)isonicotinamide;

N-(4'-{[(Cyclopropylmethyl)amino]carbonyl}-6-methyl-1,1'-biphenyl-3-yl)-2-morpholin-4-yl-isonicotinamide;

N-(4'-{[(Cyclopropylmethyl)amino]carbonyl}-6-methyl-1,1'-biphenyl-3-yl)-2-piperidin-1-yl-isonicotinamide;

N-(4'-{[(Cyclopropylmethyl)amino]carbonyl}-6-methyl-1,1'-biphenyl-3-yl)-2-dimethylaminoisonicotinamide;

2-(Cyclopropylmethylamino)-N-(4'-{[(cyclopropylmethyl)amino]carbonyl}-6-methyl-1,1'-biphenyl-3-yl-isonicotinamide;

N-(4'-{[(Cyclopropylmethyl)amino]carbonyl}-6-methyl-1,1'-biphenyl-3-yl)-2-(isobutylamino)isonicotinamide;

N-(4'-{[(Cyclopropylmethyl)amino]carbonyl}-6-methyl-1,1'-biphenyl-3-yl)-2-thiomorpholin-4-yl-isonicotinamide;

2-(Cyclohexylamino)-N-(4'-{[(cyclopropylmethyl)amino]carbonyl}-6-methyl-1,1'-biphenyl-3-yl-isonicotinamide;

2-(Cyclopropylamino)-N-(4'-{[(cyclopropylmethyl)amino]carbonyl}-6-methyl-1,1'-biphenyl-3-yl-isonicotinamide;

N-(4'-{[(Cyclopropylmethyl)amino]carbonyl}-6-methyl-1,1'-biphenyl-3-yl)-2-(diethylamino)isonicotinamide;

N-(4'-{[(Cyclopropylmethyl)amino]carbonyl}-6-methyl-1,1'-biphenyl-3-yl)-2-(4-methylpiperidin-1-yl)isonicotinamide;

N-(4'-{[(Cyclopropylmethyl)amino]carbonyl}-6-methyl-1,1'-biphenyl-3-yl)-2-(2-methylpyrrolidin-1-yl)isonicotinamide;

N-(4'-{[(Cyclopropylmethyl )amino]carbonyl}-6-methyl-1,1'-biphenyl-3-yl)-2-(3-dimethylaminopyrrolidin-1-yl)isonicotinamide;

N-(4'-{[(Cyclopropylmethyl )amino]carbonyl}-6-methyl-1,1'-biphenyl-3-yl)-2-(1,2,3,6-terrahydropyrid-1-yl)isonicotinamide; N-(4'-{[(Cyclopropylmethyl)amino]carbonyl}-6-methyl-1,1'-biphenyl-3-yl)-2-(3-methylpiperidin-1-yl)isonicotinamide;

N-(4'-{[(Cyclopropylmethyl)amino]carbonyl}-6-methyl-1,1'-biphenyl-3-yl)-2-(3,5-dimethylpiperidin-1-yl)isonicotinamide;

N-(4'-{[(Cyclopropylmethyl)amino]carbonyl}-6-methyl-1,1'-biphenyl-3-yl)-2-(2-methoxymethylpyrrolidin-1-yl)isonicotinamide;

2-(Cyclobutylamino)-N-(4'-{[(cyclopropylmethyl)amino]carbonyl}-6-methyl-1,1'-biphenyl-3-yl)isonicotinamide;

N-{4'-[(Cyclopropylamino)carbonyl]-6-methyl-1,1'-biphenyl-3-yl}-2-pyrrolidin-1-yl )isonicotinamide;

N-(4'-{[(Cyclopropylmethyl)amino]carbonyl}-6-methyl-1,1'-biphenyl-3-yl)-5-(pyrid-2-yl )thiophene-2-carboxamide;

5-(4-Chlorophenyl)-N-(4'-{[(cyclopropylmethyl)amino]carbonyl}-6-methyl-1,1'-biphenyl-3-yl)-2-furamide;

N-(4'-{[(Cyclopropylmethyl)amino]carbonyl}-6-methyl-1,1'-biphenyl-3-yl)-2-methyl-5-phenyl-3-furamide;

N-(4'-{[(Cyclopropylmethyl)amino]carbonyl}-6-methyl-1,1'-biphenyl-3-yl)-2-(pyrid-3-yl)thiazole-4-carboxamide;

N-(4'-{[(Cyclopropylmethyl)amino]carbonyl}-6-methyl-1,1'-biphenyl-3-yl)-4-methyl-2-(pyrid-3-yl)thiazole-5-carboxamide; N-(4'-{[(Cyclopropylmethyl)amino]carbonyl}-6-methyl-1,1'-biphenyl-3-yl)-1-ethyl-3-(thiophen-2-yl)pyrazole-5-carboxamide; N-(4'-{[(Cyclopropylmethyl)amino]carbonyl}-6-methyl-1,1'-biphenyl-3-yl)-2-(fur-2-yl )acetamide;

N(4'-{[(Cyclopropylmethyl)amino]carbonyl}-6-methyl-1,1'-biphenyl-3-yl)-cyclobutanecarboxamide; or a pharmaceutically acceptable salt or solvate thereof.

13. A compound according to claim 1 which is:

N-(4'-{[(Cyclopropylmethyl)amino]carbonyl}-6-methyl-1,1'-biphenyl-3-yl)-cyclopropanecarboxamide;

N-(4'-{[(Cyclopropylmethyl )amino]carbonyl}-6-methyl-1,1'-biphenyl-3-yl)-2-furamide;

N-(4'-{[(Cyclopropylmethyl)amino]carbonyl}-6-methyl-1,1'-biphenyl-3-yl)thiophene-3-carboxamide;

N-(4'-{[(Cyclopropylmethyl)amino]carbonyl}-6-methyl-1,1'-biphenyl-3-yl)-cyclopentanecarboxamide;

N-(4'-{[(Cyclopropylmethyl)amino]carbonyl}-6-methyl-1,1'-biphenyl-3-yl)terrahydropyran-4-carboxamide;

N-(4'-{[(Cyclopropylmethyl)amino]carbonyl}-6-methyl-1,1'-biphenyl-3-yl)tetrahydrofuran-2-carboxamide;

N-(4'-{[(Cyclopropylmethyl)amino]carbonyl}-6-methyl-1,1'-biphenyl-3-yl)thiazole-4-carboxamide;

N-(4'-{[(Cyclopropylmethyl)amino]carbonyl}-6-methyl-1,1'-biphenyl-3-yl)isoxazole-5-carboxamide;

5-Bromo-N-(4'-{[(cyclopropylmethyl)amino]carbonyl}-6-methyl-1,1'-biphenyl-3-yl)-nicotinamide;

N-(4'-{[(Cyclopropylmethyl)amino]carbonyl}-6-methyl-1,1'-biphenyl-3-yl)-2-phenylpyrimidine-4-carboxamide;

5-Chloro-N-(4'-{[(cyclopropylmethyl)amino]carbonyl}-6-methyl-1,1'-biphenyl-3-yl)-2-(piperidin-1-yl)pyrimidine-4-carboxamide;

5-Chloro-N-(4'-{[(cyclopropylmethyl )amino]carbonyl}-6-methyl-1,1'-biphenyl-3-yl)-2-hexamethyleneiminopyrimidine-4-carboxamide;

N-(4'-{[(Cyclopropylmethyl)amino]carbonyl}-6-methyl-1,1'-biphenyl-3-yl)-3-(2,5-dimethylpyrrol-1-yl)benzamide;

N-(4'-{[(Cyclopropylmethyl)amino]carbonyl}-6-methyl-1,1'-biphenyl-3-yl)-3-(4-trifluoromethylphenyl)benzamide;

N-(4'-{[(Cyclopropylmethyl)amino]carbonyl}-6-methyl-1,1'-biphenyl-3-yl)-4-methoxy-3-phenylbenzamide;

N-(4'-{[(Cyclopropylmethyl)amino]carbonyl}-6-methyl-1,1'-biphenyl-3-yl)-3-(2-oxo-1-pyrrolidine)benzamide;

N-(4'-{[(Cyclopropylmethyl)amino]carbonyl}-6-methyl-1,1'-biphenyl-3-yl)-3-fur-3-ylbenzamide;

2-Cyclohexyl-N-(4'-{[(cyclopropylmethyl)amino]carbonyl}-6-methyl-1,1'-biphenyl-3-yl)-6-methylquinoline-4-carboxamide;

2-Cyclopropyl-N-(4'-{[(cyclopropylmethyl)amino]carbonyl}-6-methyl-1,1'-biphenyl-3-yl )quinoline-4-carboxamide;

N-(4'-{[(Cyclopropylmethyl )amino]carbonyl}-6-methyl-1,1'-biphenyl-3-yl)-2-fur-2-ylquinoline-4-carboxamide;

N-(4'-{[(Cyclopropylmethyl)amino]carbonyl}-6-methyl-1,1'-biphenyl-3-yl)-2-methyl-3-furamide;

N-(4'-{[(Cyclopropylmethyl)amino]carbonyl}-6-methyl-1,1'-biphenyl-3-yl)-cyclopropylacetamide;

N-(4'-{[(Cyclopropylmethyl)amino]carbonyl}-6-methyl-1,1'-biphenyl-3-yl)propionamide;
N-(4'-{[(Cyclopropylmethyl)amino]carbonyl}-6-methyl-1,1'-biphenyl-3-yl)butyramide;
N-(4'-{[(Cyclopropylmethyl)amino]carbonyl}-6-methyl-1,1'-biphenyl-3-yl)acetamide
N-(4'-{[(Cyclopropylmethyl)amino]carbonyl}-6-methyl-1,1'-biphenyl-3-yl)isovaleramide;
N-(4'-{[(Cyclopropylmethyl)amino]carbonyl}-6-methyl-1,1'-biphenyl-3-yl)trifluoroacetamide;
N-(4'-{[(Cyclopropylmethyl)amino]carbonyl}-6-methyl-1,1'-biphenyl-3-yl)-6-(4-fluorophenyl)pyrazine-2-carboxamide;
N-(4'-{[(Cyclopropylmethyl )amino]carbonyl}-6-methyl-1,1'-biphenyl-3-yl)-6-morpholin-4-ylpyrazine-2-carboxamide;
N-(4'-{[(3-Dimethylaminopropyl)amino]carbonyl}-6-methyl-1,1'-biphenyl-3-yl)-3-furamide;
N-[6-Methyl-4'-({[2-(methylsulphonylamino)ethyl]amino}carbonyl)-1,1'-biphenyl-3-yl]-3-furamide;
N-(4'-{[(2-Hydroxyethyl)amino]carbonyl}-6-methyl-1,1'-biphenyl-3-yl)-3-furamide;
N-(4'-{[(3-Hydroxypropyl)amino]carbonyl}-6-methyl-1,1'-biphenyl-3-yl)-3-furamide;
N-(4'-{[(Cyclopropylmethyl)amino]carbonyl}-6-methyl-1,1'-biphenyl-3-yl)thiophene-2-carboxamide;
N-(4'-{[(Cyclopropylmethyl)amino]carbonyl}-6-methyl-1,1'-biphenyl-3-yl)benzamide;
N-(4'-{[(Cyclopropylmethyl )amino]carbonyl}-6-methyl-1,1'-biphenyl-3-yl)-5-(3-chlorophenyl)-2-furamide;
N-(6-Chloro-4'-{[(cyclopropylmethyl)amino]carbonyl}-1,1'-biphenyl-3-yl)-3-furamide;
N-(4'-{[(4-Hydroxybutyl)amino]carbonyl}-6-methyl-1,1'-biphenyl-3-yl)-3-furamide;
N-(4'-{[(4-Hydroxybutyl)amino]carbonyl}-6-methyl-1,1'-biphenyl-3-yl)thiophene-3-carboxamide;
N-(4'-{[(3-Hydroxypropyl)amino]carbonyl}-6-methyl-1,1'-biphenyl-3-yl)thiophene-3-carboxamide;
N-(4'-{[(2-Hydroxyethyl)amino]carbonyl}-6-methyl-1,1'-biphenyl-3-yl)thiophene-3-carboxamide; or
a pharmaceutically acceptable salt or solvate thereof.

* * * * *